US010308915B2

(12) United States Patent
Yuan et al.

(10) Patent No.: US 10,308,915 B2
(45) Date of Patent: Jun. 4, 2019

(54) GENES AND USES THEREOF, METHODS FOR SYNTHESIZING ODD NUMBERED MEDIUM CHAIN ALIPHATIC ALDEHYDES AND METHODS FOR SYNTHESIZING EVEN NUMBERED MEDIUM CHAIN ALIPHATIC HYDROCARBONS

(71) Applicant: Tianjin University, Tianjin (CN)

(72) Inventors: Yingjin Yuan, Tianjin (CN); Yingxiu Cao, Tianjin (CN); Wenhai Xiao, Tianjin (CN); Duo Liu, Tianjin (CN); Mingzhu Ding, Tianjin (CN); Zexiong Xie, Tianjin (CN); Jinlai Zhang, Tianjin (CN)

(73) Assignee: TIANJIN UNIVERSITY, Tianjin (CN)

(*) Notice: Subject to any disclaimer, the term of this patent is extended or adjusted under 35 U.S.C. 154(b) by 43 days.

(21) Appl. No.: 15/516,480

(22) PCT Filed: Sep. 9, 2015

(86) PCT No.: PCT/CN2015/089232
§ 371 (c)(1),
(2) Date: Apr. 3, 2017

(87) PCT Pub. No.: WO2016/062171
PCT Pub. Date: Apr. 28, 2016

(65) Prior Publication Data
US 2018/0273918 A1 Sep. 27, 2018

(30) Foreign Application Priority Data
Oct. 22, 2014 (CN) .......................... 2014 1 0566258

(51) Int. Cl.
| | |
|---|---|
| *C12N 9/02* | (2006.01) |
| *C12N 9/16* | (2006.01) |
| *C12N 9/88* | (2006.01) |
| *C12N 9/04* | (2006.01) |
| *C12P 5/02* | (2006.01) |
| *C12P 7/24* | (2006.01) |
| *C12P 7/04* | (2006.01) |

(52) U.S. Cl.
CPC ......... *C12N 9/0083* (2013.01); *C12N 9/0006* (2013.01); *C12N 9/16* (2013.01); *C12N 9/88* (2013.01); *C12P 5/02* (2013.01); *C12P 7/04* (2013.01); *C12P 7/24* (2013.01); *C12Y 101/01021* (2013.01); *C12Y 401/99005* (2013.01)

(58) Field of Classification Search
CPC ......... C12N 9/0083; C12N 9/88; C12N 9/16; C12N 9/0006; C12Y 401/99005; C12Y 101/01021; C12P 5/02; C12P 7/24; C12P 7/04
See application file for complete search history.

(56) References Cited

U.S. PATENT DOCUMENTS 10,017,790 B2 * 7/2018 Sporleder ............ C12N 9/0069
2011/0263885 A1   10/2011 Korlipara et al.
2013/0149756 A1   6/2013 Sporleder et al.

FOREIGN PATENT DOCUMENTS

| CN | 101490241 A | 7/2009 |
| CN | 102089270 A | 6/2011 |
| CN | 102586350 A | 7/2012 |

OTHER PUBLICATIONS

Akthar et al., Carboxylic acid reductase is a versatile enzyme for the conversion of fatty acids into fuels and chemical commodities. PNAS., 2013, vol. 110(1): 87-92. (Year: 2013).*
Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Kaehne et al., A recombinant a-dioxygenase from rice to produce fatty aldehydes in E.coli. Appl. Microbiol. Biotechno., 2011, vol. 90: 989-995. (Year: 2011).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Akhtar et al., Carboxylic acid reductase is a versatile enzyme for the conversion of fatty acids into fuels and chemical commodities, PNAS, Jan. 2, 2013, vol. 110, No. 1, 87-92.
International Search Report issued in PCT/CN2015/089232 dated Dec. 28, 2015, 9 pages.
Zhu et al., Crystal structures of α-dioxygenase from *Oryza sativa*: Insights into substrate binding and activation by hydrogen peroxide, Protein Science 2013, vol. 22:1432-1438.

(Continued)

*Primary Examiner* — Ganapathirama Raghu
(74) *Attorney, Agent, or Firm* — RatnerPrestia

(57) ABSTRACT

Provided are genes, coding proteins and uses thereof, gene elements, genes and uses, gene elements, methods for synthesizing odd numbered medium chain aliphatic aldehydes, for synthesizing odd numbered medium chain aliphatic alcohol and for synthesizing even numbered medium chain aliphatic hydrocarbons. Provided is method for producing odd numbered aliphatic alcohols in *Escherichia coli*. An α-dioxygenase from rice is used without additional deoxidization and energy supply from cells. The α-dioxygenase can also be used for synthesizing aliphatic alcohols with different proportions of C11 to C15 by co-working with different thioesterases.

6 Claims, 7 Drawing Sheets

Specification includes a Sequence Listing.

(56) References Cited

OTHER PUBLICATIONS

Cao et al., Biosynthesis of odd-chain fatty alcohols in *Escherichia coli*, Metabolic Engineering 29 (2015) 113-123.
Cao, Biosynthesis of alkanes and fatty alcohols in *E. coli* through moduler design, Nov. 2013, Abstract and partial English translation, 126 pages.
Os12g0448900 [*Oryza sativa* Japonica Group ] NCBI Reference Sequence NP_001066718.1, NCBI GenBank Jun. 8, 2010, 1 page.
Chinese First Office Action issued in CN 201410566258.8 dated Jul. 4, 2018, with English translation, 13 pages.

* cited by examiner

SEQUENCE LISTING

```
<160> NUMBER OF SEQ ID NOS: 77

<210> SEQ ID NO 1
<211> LENGTH: 1860
<212> TYPE: DNA
<213> ORGANISM: Artificial
<220> FEATURE:
<223> OTHER INFORMATION: Synthesized sequence for dioxygenase

<400> SEQUENCE: 1
atgggcagcg gtttattcaa acctcgcgtt catccggacc tgcgcgacgt gttcagcaaa      60
atgagttttt ttgataaaat cggctttctg ttcatccatg ccttcgacaa gcgcaactta     120
tggcacaaag tgcctgtgcc gatcggcctg ctgtatctga ataccgccg caccttactg     180 gaaaagtata atctgctggc cgttggccgt agcagtcatg gtgcactgtt cgacccgaaa     240
gaatttctgt accgcaccga ggacggtaaa tacaatgacc cgcacaacgc cgaggccggc     300
agccaaaaca cctttttttgg ccgcaacatg gaaccggttg accagcagga cgagttaatg     360
agccctgatc cgttcgtggt ggcaaccaaa ctgctggccc gtcgcgagta caaggataca     420
ggtaaacagt taacattct ggccgccgcc tggattcagt tcatggttca cgactggatg     480
gaccacatgg aggacacagg ccagattggt atcacagcac cgaaggaggt tgccaatgaa     540
tgccctctga agagcttcaa gttccacccg accaaggaac tgccgacaaa tagtgacggc     600
attaaaattg gccactataa catccgtaca gcctggtggg atggtagcgc cgtgtacggc     660
aataatgagg aacgcgccga gaagctgcgc acctatgttg acggcaagtt agtgattggc     720
gacgacggtc tgctgttaca caaggagaac ggcgtggcat taagtggcga tatccgtaac     780
agttgggccg gcgttagcat tctgcaagcc ctgtttgtta aggaacataa cgccgtgtgc     840
gatgccatta aggaggagca tccgaatctg agcgacgaag agctgtaccg ttacgccaag     900
ctggtgacaa gcgcagtgat cgccaaggtg cacaccatcg actggacagt tgaactgctg     960
aagaccaaaa ccatgcgcgc cgccatgcgt gcaaactggt acggcctgct gggcaagaag    1020
atcaaagaca cctttggcca tatcggcggc ccgatttag gtggcttagt gggtctgaaa    1080
aagccgaata atcatggcgt gccttacagc ctgaccgaag agttcaccag cgtttaccgc    1140
atgcatagcc tgatccctag tacactgaag ttacgcgacc ctaccggtca gccggatgcc    1200
aataatagtc ctccttgcct ggaggacatc gacatcggtg aaatgatcgg tctgaagggc    1260
gaggaacaac tgagcaagat cggttttgag aagcaggcct taagcatggg ttatcaggcc    1320
tgcggcgccc tggagctgtg gaactaccct agcttcttcc gcaacttaat cccgcaaaac    1380
ctggacggca ccaatcgtag tgaccgcatt gatctggcag cactggaggt ttatcgtgac    1440
cgcgagcgta gcgttcctcg ctacaacgag ttccgccgcc gcctgttcct gatcccgatt    1500
```

```
aagagctggg aagacctgac cagcgacaaa gacgccatcg agacaatccg cgcaatctat    1560
ggcgacgacg tggagaaact ggacctgctg gtgggcctga tggccgaaaa gaaaattaaa    1620
ggcttcgcaa ttagcgaaac agcctttaat atctttatcc tgatggcaag ccgtcgttta    1680
gaggccgacc gtttcttcac cagtaacttc aacgaggaga catacaccaa gaagggcatg    1740
caatgggtga aaaccaccga aggcctgcgc gatgtgatca accgccatta cccggagatc    1800
accgccaaat ggatgaagag cagcagtgcc tttagcgtgt gggatgcaga ctattaataa    1860
```

<210> SEQ ID NO 2
<211> LENGTH: 1011
<212> TYPE: DNA
<213> ORGANISM: Artificial
<220> FEATURE:
<223> OTHER INFORMATION: Synthesized sequence for aldehyde dehydrogenase

<400> SEQUENCE: 2

```
atgatcaagg cttacgctgc tctggaagct aacggtaaac tccagccgtt cgaatacgac      60
ccgggtgctc tgggtgctaa cgaagttgaa atcgaagttc agtactgcgg tgtttgccac     120
tctgacctgt ctatgatcaa caacgaatgg ggtatctcta actacccgct ggttccgggt     180
cacgaagttg ttggaaccgt tgctgctatg ggtgaaggtg ttaaccacgt tgaagttggt     240
gacctggttg gtctgggttg cactctggt  tactgcatga cctgccactc ttgcctgtct     300
ggttaccaca acctgtgcgc taccgctgaa tctaccatcg ttggtcacta cggcggcttc     360
ggtgaccgtg ttcgtgctaa aggtgtttct gttgttaaac tgccgaaagg tatcgacctg     420
gcttctgctg gtccgctgtt ctgcggcggt ataaccgtgt tcagcccgat ggttgaactg     480
tctctgaaac cgaccgctaa agttgctgtt atcggtatcg gtggtctggg tcacctggct     540
gttcagttcc tgcgtgcttg gggttgcgaa gttaccgctt tcacctcttc tgctcgtaaa     600
cagaccgaag ttctggaact gggtgctcac cacatcctgg actctaccaa cccggaagct     660
atcgcttctg ctgaaggtaa attcgactac atcatctcta ccgttaacct gaaactggac     720
tggaacctgt acatctctac cctggctccg cagggtcact tccacttcgt tggtgttgtt     780
ctggaaccgc tggacctgaa cctgttcccg ctgctgatgg gtcagcgttc tgtttctgct     840
tctccggttg gttctccggc taccatcgct accatgctgg acttcgctgt cgtcacgac     900 atcaaaccgg ttgttgaaca gttctctttc gaccagatca cgaagctat cgctcacctg     960 gaatctggta agctcacta ccgtgttgtt ctgtctcact ctaaaaacta a             1011
```

<210> SEQ ID NO 3
<211> LENGTH: 1878
<212> TYPE: DNA
<213> ORGANISM: Artificial
<220> FEATURE:
<223> OTHER INFORMATION: Synthesized sequence for aldehyde decarbonylase

<400> SEQUENCE: 3

```
atggctacca aaccgggtgt tctgaccgac tggccgtgga ccccgctcgg cagcttcaaa      60
tacatcgtta tcgctccgtg ggctgttcac tctacctacc gtttcgttac cgacgacccg     120
gaaaaacgtg acctgggtta cttcctggtt ttcccgttcc tgctgttccg tatcctccac     180
aatcaggtgt ggatcagcct gtctcgttac tacacctctt ctggtaaacg tcgtatcgtt     240
gacaaaggta tcgacttcaa ccaggttgac cgtgaaacca actgggacga ccagatcctg     300
ttcaacggtg ttctgttcta catcggtatc aacctgctgc cggaagctaa acagctcccg     360
```

-continued

```
tggtggcgta ccgacggtgt tctgatggct gctctgatcc acaccggtcc ggttgaattt      420
ctgtactact ggctgcacaa agctctgcac caccacttcc tgtactctcg ttaccactct      480
caccaccact cttctatcgt taccgaaccg atcacctctg ttatccaccc gttcgctgaa      540
cacatcgctt acttcatcct gttcgctatc ccgctgctga ccaccctgct gaccaaaacc      600
gcttctatca tctctttcgc tggttacatc atctacatcg acttcatgaa caacatgggt      660
cactgcaact tcgaactgat cccgaaacgt ctgttccacc tgttcccgcc gctgaaattc      720
ctgtgctaca ccccgtctta ccactctctg caccacaccc agttccgtac caactactct      780
ctgttcatgc cgctgtacga ctacatctac ggtactatgg acgaatctac cgacaccctg      840
tacgaaaaaa ccctggaacg tggtgacgac atcgttgacg ttgttcacct gacccacctg      900
accaccccgg aatctatcta ccacctgcgt atcggtctgg cttctttcgc ttcttacccg      960
ttcgcttacc gttggttcat cgtctgctg tggccgttca cctctctgtc tatgatcttc      1020
accctgttct acgctcgtct gttcgttgcg gagcgtaaca gcttcaacaa actgaatctg      1080
caatcttggg ttatcccgcg ttacaacctg caataccgtc tgaaatggcg taaagaagct      1140
atcaacaaca tgatcgaaaa agctatcctg gaagctgaca aaaaaggtgt taaagttctg      1200
tctctgggtc tgatgaacca gggtgaagaa ctgaaccgta atggcgaagt atacatccac      1260 aaccaccccgg acatgaaagt tcgtctggtt gacggttctc gtctggctgc tgctgttgtt      1320
atcaactctg ttccgaaagc taccacctct gttgttatga ccggtaacct gaccaaagtt      1380
gcttacacca tcgcttctgc tctgtgccag cgtggtgttc aggtttctac cctgcgtctg      1440
gacgaatacg aaaaaatccg ttcttgcgtt ccgcaggaat gccgtgacca cctggtttac      1500
ctgacctctg aagctctgtc ttctaacaaa gtttggctgg ttggtgaagg tactacccgt      1560
gaagaacagg aaaaagctac caaaggtact ctgttcatcc cgttctctca gttcccgctg      1620
aaacagctcc gtcgtgactg catctaccac accaccccgg ctctgatcgt tccgaaatct      1680
ctggttaacg ttcactcttg cgaaaactgg ctgccgcgta agctatgtc tgctaccgt       1740 gttgctggta tcctgcacgc tctggaaggt tgggaaatgc acgaatgcgg tacttctctg      1800
ctgctgtctg acctcgacca ggtctgggaa gcgtgcctgt cgcatggctt ccagccgctg      1860
ctcctgccgc accactaa                                                     1878
```

<210> SEQ ID NO 4
<211> LENGTH: 732
<212> TYPE: DNA
<213> ORGANISM: Artificial
<220> FEATURE:
<223> OTHER INFORMATION: Synthesized sequence for aldehyde decarbonylase

<400> SEQUENCE: 4

```
atgccgaccc tggaaatgcc ggtggctgcg gttctggatt ctacggttgg ctcgtctgaa       60
gcactgccgg actttacctc tgatcgctat aaagatgcct acagccgtat caacgcaatt      120
gttatcgaag gcgaacagga agctcatgat aattatattg cgattggcac cctgctgccg      180
gaccacgtcg aagaactgaa acgtctggct aaaatggaaa tgcgccataa gaaaggcttt      240
acggcgtgcg gcaaaaacct gggtgtggaa gcagatatgg actttgctcg tgaatttttc      300
gcgccgctgc gcgataattt ccagaccgct ctgggccaag gtaaaacccc gacgtgtctg      360
ctgattcaag ccctgctgat cgaagcattt gctattagcg catatcatac gtacatcccg      420
gtttctgatc cgttcgcacg caaaattacc gaaggcgtgg ttaaagacga atatacgcac      480
ctgaactacg gtgaagcgtg gctgaaagcc aatctggaaa gttgccgtga agaactgctg      540
```

```
gaagccaacc gcgaaaatct gccgctgatt cgtcgcatgc tggatcaggt cgcaggtgac    600
gcggcggtgc tgcaaatgga taaagaagac ctgatcgaag atttcctgat tgcctaccag    660
gaatccctga cggaaatcgg cttcaatacc cgcgaaatca cccgcatggc agcagcagca    720
ctggttagct aa                                                        732
```

```
<210> SEQ ID NO 5
<211> LENGTH: 699
<212> TYPE: DNA
<213> ORGANISM: Artificial
<220> FEATURE:
<223> OTHER INFORMATION: Synthesized sequence for aldehyde decarbonylase

<400> SEQUENCE: 5
atgccgcagc tggaagcgag cctggaactg gattttcaga gcgaaagcta taaagatgcg     60
tatagccgta ttaacgcgat tgtgattgaa ggcgaacagg aagcgtttga taactataac    120
cgtctggcgg aaatgctgcc ggatcagcgt gatgaactgc ataaactggc gaaaatggaa    180
cagcgtcaca tgaaaggctt tatggcgtgc ggcaaaaacc tgagcgtgac cccggatatg    240
ggctttgcgc agaaattttt tgaacgtctg catgaaaact ttaaagcggc ggcggcggaa    300
ggcaaagtgg tgacctgcct gctgattcag agcctgatta ttgaatgctt tgcgattgcg    360
gcgtataaca tttatattcc ggtggcggat gcgtttgcgc gtaaaattac cgaaggcgtg    420
gtgcgtgatg aatatctgca tcgtaacttt ggcgaagaat ggctgaaagc gactttgat    480 gcgagcaaag cggaactgga agaagcgaac cgtcagaacc tgccgctggt gtggctgatg    540
ctgaacgaag tggcggatga tgcgcgtgaa ctgggcatgg aacgtgaaag cctggtggaa    600
gattttatga ttgcgtatgg cgaagcgctg gaaaacattg gctttaccac ccgtgaaatt    660
atgcgtatga gcgcgtatgg cctggcggcg gtgtaataa                           699
```

```
<210> SEQ ID NO 6
<211> LENGTH: 29
<212> TYPE: DNA
<213> ORGANISM: Artificial
<220> FEATURE:
<223> OTHER INFORMATION: Synthesized primer

<400> SEQUENCE: 6
cctccatggc ggacacgtta ttgattctg                                       29
```

```
<210> SEQ ID NO 7
<211> LENGTH: 38
<212> TYPE: DNA
<213> ORGANISM: Artificial
<220> FEATURE:
<223> OTHER INFORMATION: Synthesized primer

<400> SEQUENCE: 7
ccgggatccg aatactagtt atgagtcatg atttacta                             38
```

```
<210> SEQ ID NO 8
<211> LENGTH: 24
<212> TYPE: DNA
<213> ORGANISM: Artificial
<220> FEATURE:
<223> OTHER INFORMATION: Synthesized primer

<400> SEQUENCE: 8
acagcgccgc tgagaaaaag cgaa                                            24
```

<210> SEQ ID NO 9
<211> LENGTH: 20
<212> TYPE: DNA
<213> ORGANISM: Artificial
<220> FEATURE:
<223> OTHER INFORMATION: Synthesized primer

<400> SEQUENCE: 9
agttcggcat ggggtcaggt                                            20

<210> SEQ ID NO 10
<211> LENGTH: 24
<212> TYPE: DNA
<213> ORGANISM: Artificial
<220> FEATURE:
<223> OTHER INFORMATION: Synthesized primer

<400> SEQUENCE: 10
ggcccttaag tcgaacagaa agta                                       24

<210> SEQ ID NO 11
<211> LENGTH: 29
<212> TYPE: DNA
<213> ORGANISM: Artificial
<220> FEATURE:
<223> OTHER INFORMATION: Synthesized primer

<400> SEQUENCE: 11
tatctgcagc ataagggaga gcgtcgaga                                  29

<210> SEQ ID NO 12
<211> LENGTH: 46
<212> TYPE: DNA
<213> ORGANISM: Artificial
<220> FEATURE:
<223> OTHER INFORMATION: Synthesized primer

<400> SEQUENCE: 12
tctcgacgct ctcccttatg ctgcagacat cataacggtt ctggca               46

<210> SEQ ID NO 13
<211> LENGTH: 46
<212> TYPE: DNA
<213> ORGANISM: Artificial
<220> FEATURE:
<223> OTHER INFORMATION: Synthesized primer

<400> SEQUENCE: 13
tacgattact ttctgttcga cttaagggcg gatttgtcct actcag                46

<210> SEQ ID NO 14
<211> LENGTH: 20
<212> TYPE: DNA
<213> ORGANISM: Artificial
<220> FEATURE:
<223> OTHER INFORMATION: Synthesized primer

<400> SEQUENCE: 14
gtccatgtgc tggcgttcaa                                            20

<210> SEQ ID NO 15
<211> LENGTH: 20
<212> TYPE: DNA
<213> ORGANISM: Artificial
<220> FEATURE:
<223> OTHER INFORMATION: Synthesized primer -continued

```
<400> SEQUENCE: 15
gattatgcgg ccgtgtacaa                                                 20

<210> SEQ ID NO 16
<211> LENGTH: 28
<212> TYPE: DNA
<213> ORGANISM: Artificial
<220> FEATURE:
<223> OTHER INFORMATION: Synthesized primer

<400> SEQUENCE: 16
acaggcatat gggcagcggt ttattcaa                                        28

<210> SEQ ID NO 17
<211> LENGTH: 38
<212> TYPE: DNA
<213> ORGANISM: Artificial
<220> FEATURE:
<223> OTHER INFORMATION: Synthesized primer

<400> SEQUENCE: 17
gggggatccg aatactagtt attaatagtc tgcatccc                             38

<210> SEQ ID NO 18
<211> LENGTH: 20
<212> TYPE: DNA
<213> ORGANISM: Artificial
<220> FEATURE:
<223> OTHER INFORMATION: Synthesized primer

<400> SEQUENCE: 18
tcttccccat cggtgatgtc                                                 20

<210> SEQ ID NO 19
<211> LENGTH: 23
<212> TYPE: DNA
<213> ORGANISM: Artificial
<220> FEATURE:
<223> OTHER INFORMATION: Synthesized primer

<400> SEQUENCE: 19
tcacgctgcg cgtaaccacc aca                                             23

<210> SEQ ID NO 20
<211> LENGTH: 28
<212> TYPE: DNA
<213> ORGANISM: Artificial
<220> FEATURE:
<223> OTHER INFORMATION: Synthesized primer

<400> SEQUENCE: 20
ggggacatat gaaggctgca gttgttac                                        28

<210> SEQ ID NO 21
<211> LENGTH: 38
<212> TYPE: DNA
<213> ORGANISM: Artificial
<220> FEATURE:
<223> OTHER INFORMATION: Synthesized primer

<400> SEQUENCE: 21
gagggatccg aatactagtt agtgacggaa atcaatca                             38

<210> SEQ ID NO 22
```

```
<211> LENGTH: 29
<212> TYPE: DNA
<213> ORGANISM: Artificial
<220> FEATURE:
<223> OTHER INFORMATION: Synthesized primer

<400> SEQUENCE: 22
ggggcatatg tcgatgataa aaagctatg                                    29

<210> SEQ ID NO 23
<211> LENGTH: 30
<212> TYPE: DNA
<213> ORGANISM: Artificial
<220> FEATURE:
<223> OTHER INFORMATION: Synthesized primer

<400> SEQUENCE: 23
gggactagtt atcaataatc ggctttcaac                                   30

<210> SEQ ID NO 24
<211> LENGTH: 27
<212> TYPE: DNA
<213> ORGANISM: Artificial
<220> FEATURE:
<223> OTHER INFORMATION: Synthesized primer

<400> SEQUENCE: 24
ggggcatatg aacaacttta atctgca                                      27

<210> SEQ ID NO 25
<211> LENGTH: 19
<212> TYPE: DNA
<213> ORGANISM: Artificial
<220> FEATURE:
<223> OTHER INFORMATION: Synthesized primer

<400> SEQUENCE: 25
tgcgttgccc agtcctgcg                                               19

<210> SEQ ID NO 26
<211> LENGTH: 39
<212> TYPE: DNA
<213> ORGANISM: Artificial
<220> FEATURE:
<223> OTHER INFORMATION: Synthesized primer

<400> SEQUENCE: 26
cgcaggactg ggcaacgcac atgctgggcc acgaactga                         39

<210> SEQ ID NO 27
<211> LENGTH: 28
<212> TYPE: DNA
<213> ORGANISM: Artificial
<220> FEATURE:
<223> OTHER INFORMATION: Synthesized primer

<400> SEQUENCE: 27
gggactagtt agcgggcggc ttcgtata                                     28

<210> SEQ ID NO 28
<211> LENGTH: 27
<212> TYPE: DNA
<213> ORGANISM: Artificial
<220> FEATURE:
<223> OTHER INFORMATION: Synthesized primer

<400> SEQUENCE: 28
```
ggttcatatg gctgttacta atgtcgc                                        27

<210> SEQ ID NO 29
<211> LENGTH: 20
<212> TYPE: DNA
<213> ORGANISM: Artificial
<220> FEATURE:
<223> OTHER INFORMATION: Synthesized primer

<400> SEQUENCE: 29
gcgtgagtta ctgcgtccag                                                20

<210> SEQ ID NO 30
<211> LENGTH: 41
<212> TYPE: DNA
<213> ORGANISM: Artificial
<220> FEATURE:
<223> OTHER INFORMATION: Synthesized primer

<400> SEQUENCE: 30
ctggacgcag taactcacgc gatggaagct tatgtttctg t                         41

<210> SEQ ID NO 31
<211> LENGTH: 33
<212> TYPE: DNA
<213> ORGANISM: Artificial
<220> FEATURE:
<223> OTHER INFORMATION: Synthesized primer

<400> SEQUENCE: 31
gggactagtt aagcggattt tttcgctttt ttc                                  33

<210> SEQ ID NO 32
<211> LENGTH: 27
<212> TYPE: DNA
<213> ORGANISM: Artificial
<220> FEATURE:
<223> OTHER INFORMATION: Synthesized primer

<400> SEQUENCE: 32
ggtacatatg atcaaggctt acgctgc                                        27

<210> SEQ ID NO 33
<211> LENGTH: 28
<212> TYPE: DNA
<213> ORGANISM: Artificial
<220> FEATURE:
<223> OTHER INFORMATION: Synthesized primer

<400> SEQUENCE: 33
gggactagtt agtttttaga gtgagaca                                       28

<210> SEQ ID NO 34
<211> LENGTH: 27
<212> TYPE: DNA
<213> ORGANISM: Artificial
<220> FEATURE:
<223> OTHER INFORMATION: Synthesized primer

<400> SEQUENCE: 34
gtttcatatg gctaccaaac cgggtgt                                        27

<210> SEQ ID NO 35
<211> LENGTH: 28
<212> TYPE: DNA

```
<213> ORGANISM: Artificial
<220> FEATURE:
<223> OTHER INFORMATION: Synthesized primer

<400> SEQUENCE: 35
aatactagtt agtggtgcgg caggagca                                          28

<210> SEQ ID NO 36
<211> LENGTH: 27
<212> TYPE: DNA
<213> ORGANISM: Artificial
<220> FEATURE:
<223> OTHER INFORMATION: Synthesized primer

<400> SEQUENCE: 36
ttttcatatg ccgaccctgg aaatgcc                                           27

<210> SEQ ID NO 37
<211> LENGTH: 30
<212> TYPE: DNA
<213> ORGANISM: Artificial
<220> FEATURE:
<223> OTHER INFORMATION: Synthesized primer

<400> SEQUENCE: 37
ggtactagtt agctaaccag tgctgctgct                                        30

<210> SEQ ID NO 38
<211> LENGTH: 28
<212> TYPE: DNA
<213> ORGANISM: Artificial
<220> FEATURE:
<223> OTHER INFORMATION: Synthesized primer

<400> SEQUENCE: 38
atatacatat gccgcagctg gaagcgag                                          28

<210> SEQ ID NO 39
<211> LENGTH: 28
<212> TYPE: DNA
<213> ORGANISM: Artificial
<220> FEATURE:
<223> OTHER INFORMATION: Synthesized primer

<400> SEQUENCE: 39
aatactagtt attaccgc cgccaggc                                            28

<210> SEQ ID NO 40
<211> LENGTH: 28
<212> TYPE: DNA
<213> ORGANISM: Artificial
<220> FEATURE:
<223> OTHER INFORMATION: Synthesized primer

<400> SEQUENCE: 40
aaccacatat gcagcagctg accgatca                                          28

<210> SEQ ID NO 41
<211> LENGTH: 28
<212> TYPE: DNA
<213> ORGANISM: Artificial
<220> FEATURE:
<223> OTHER INFORMATION: Synthesized primer

<400> SEQUENCE: 41
gggactagtt atgcaccaat cagaccat                                          28
```

<210> SEQ ID NO 42
<211> LENGTH: 24
<212> TYPE: DNA
<213> ORGANISM: Artificial
<220> FEATURE:
<223> OTHER INFORMATION: Synthesized primer

<400> SEQUENCE: 42
ggcccttaag tcgaacagaa agta                                          24

<210> SEQ ID NO 43
<211> LENGTH: 29
<212> TYPE: DNA
<213> ORGANISM: Artificial
<220> FEATURE:
<223> OTHER INFORMATION: Synthesized primer

<400> SEQUENCE: 43
tatctgcagc ataagggaga gcgtcgaga                                     29

<210> SEQ ID NO 44
<211> LENGTH: 29
<212> TYPE: DNA
<213> ORGANISM: Artificial
<220> FEATURE:
<223> OTHER INFORMATION: Synthesized primer

<400> SEQUENCE: 44
aaactgcagc ctttcgtctt cacctcgag                                     29

<210> SEQ ID NO 45
<211> LENGTH: 22
<212> TYPE: DNA
<213> ORGANISM: Artificial
<220> FEATURE:
<223> OTHER INFORMATION: Synthesized primer

<400> SEQUENCE: 45
ttgagctcgc atgcggatcc tt                                            22

<210> SEQ ID NO 46
<211> LENGTH: 24
<212> TYPE: DNA
<213> ORGANISM: Artificial
<220> FEATURE:
<223> OTHER INFORMATION: Synthesized primer

<400> SEQUENCE: 46
aatctgcagc cgatggcgcg ccga                                          24

<210> SEQ ID NO 47
<211> LENGTH: 30
<212> TYPE: DNA
<213> ORGANISM: Artificial
<220> FEATURE:
<223> OTHER INFORMATION: Synthesized primer

<400> SEQUENCE: 47
tcgacttaag cgttcaccga caaacaacag                                    30

<210> SEQ ID NO 48
<211> LENGTH: 46
<212> TYPE: DNA
<213> ORGANISM: Artificial
<220> FEATURE:

<223> OTHER INFORMATION: Synthesized primer

<400> SEQUENCE: 48
tctcgacgct ctcccttatg ctgcagacat cataacggtt ctggca                  46

<210> SEQ ID NO 49
<211> LENGTH: 46
<212> TYPE: DNA
<213> ORGANISM: Artificial
<220> FEATURE:
<223> OTHER INFORMATION: Synthesized primer

<400> SEQUENCE: 49
tacgattact ttctgttcga cttaagggcg gatttgtcct actcag                  46

<210> SEQ ID NO 50
<211> LENGTH: 44
<212> TYPE: DNA
<213> ORGANISM: Artificial
<220> FEATURE:
<223> OTHER INFORMATION: Synthesized primer

<400> SEQUENCE: 50
tctcgacgct ctcccttatg ctgcagcctg tcaaatggac gaag                    44

<210> SEQ ID NO 51
<211> LENGTH: 28
<212> TYPE: DNA
<213> ORGANISM: Artificial
<220> FEATURE:
<223> OTHER INFORMATION: Synthesized primer

<400> SEQUENCE: 51
cggatcatat ggcggacacg ttattgat                                      28

<210> SEQ ID NO 52
<211> LENGTH: 30
<212> TYPE: DNA
<213> ORGANISM: Artificial
<220> FEATURE:
<223> OTHER INFORMATION: Synthesized primer

<400> SEQUENCE: 52
ccccggtacc ttatgagtca tgatttacta                                    30

<210> SEQ ID NO 53
<211> LENGTH: 25
<212> TYPE: DNA
<213> ORGANISM: Artificial
<220> FEATURE:
<223> OTHER INFORMATION: Synthesized primer

<400> SEQUENCE: 53
gcgccatggg cagcggttta ttcaa                                         25

<210> SEQ ID NO 54
<211> LENGTH: 44
<212> TYPE: DNA
<213> ORGANISM: Artificial
<220> FEATURE:
<223> OTHER INFORMATION: Synthesized primer

<400> SEQUENCE: 54
agggaattca aaggaggcca tcctatggcg gacacgttat tgat                    44

```
<210> SEQ ID NO 55
<211> LENGTH: 27
<212> TYPE: DNA
<213> ORGANISM: Artificial
<220> FEATURE:
<223> OTHER INFORMATION: Synthesized primer

<400> SEQUENCE: 55
cccgagctct tatgagtcat gatttac                                        27

<210> SEQ ID NO 56
<211> LENGTH: 44
<212> TYPE: DNA
<213> ORGANISM: Artificial
<220> FEATURE:
<223> OTHER INFORMATION: Synthesized primer

<400> SEQUENCE: 56
ggaaagtcga caaggaggat tataatggcg ctggaatgga aacc                     44

<210> SEQ ID NO 57
<211> LENGTH: 31
<212> TYPE: DNA
<213> ORGANISM: Artificial
<220> FEATURE:
<223> OTHER INFORMATION: Synthesized primer

<400> SEQUENCE: 57
ttttgaagct tttacacacg cggttccgcc g                                   31

<210> SEQ ID NO 58
<211> LENGTH: 45
<212> TYPE: DNA
<213> ORGANISM: Artificial
<220> FEATURE:
<223> OTHER INFORMATION: Synthesized primer

<400> SEQUENCE: 58
ggaaagtcga caaggaggcc atcctatgct gaaactgagc tgtaa                    45

<210> SEQ ID NO 59
<211> LENGTH: 35
<212> TYPE: DNA
<213> ORGANISM: Artificial
<220> FEATURE:
<223> OTHER INFORMATION: Synthesized primer

<400> SEQUENCE: 59
cagggaagct tttagcggga ggatttttta cgcca                               35

<210> SEQ ID NO 60
<211> LENGTH: 32
<212> TYPE: DNA
<213> ORGANISM: Artificial
<220> FEATURE:
<223> OTHER INFORMATION: Synthesized primer

<400> SEQUENCE: 60
cgttccatgg cgacgcaatt tgcatttgtg tt                                  32

<210> SEQ ID NO 61
<211> LENGTH: 47
<212> TYPE: DNA
<213> ORGANISM: Artificial
<220> FEATURE:
<223> OTHER INFORMATION: Synthesized primer
```

<400> SEQUENCE: 61
aaggatccga atactagtta aagctccagc gccgctgcca tcgctga         47

<210> SEQ ID NO 62
<211> LENGTH: 32
<212> TYPE: DNA
<213> ORGANISM: Artificial
<220> FEATURE:
<223> OTHER INFORMATION: Synthesized primer

<400> SEQUENCE: 62
gggtccatgg cgaattttga aggaaaaatc gc         32

<210> SEQ ID NO 63
<211> LENGTH: 39
<212> TYPE: DNA
<213> ORGANISM: Artificial
<220> FEATURE:
<223> OTHER INFORMATION: Synthesized primer

<400> SEQUENCE: 63
aaggatccga atactagtta gaccatgtac atcccgccg         39

<210> SEQ ID NO 64
<211> LENGTH: 25
<212> TYPE: DNA
<213> ORGANISM: Artificial
<220> FEATURE:
<223> OTHER INFORMATION: Synthesized primer

<400> SEQUENCE: 64
ggtccatggt agataaacgc gaatc         25

<210> SEQ ID NO 65
<211> LENGTH: 39
<212> TYPE: DNA
<213> ORGANISM: Artificial
<220> FEATURE:
<223> OTHER INFORMATION: Synthesized primer

<400> SEQUENCE: 65
aaggatccga atactagtta gaaggcagac gtatcctgg         39

<210> SEQ ID NO 66
<211> LENGTH: 26
<212> TYPE: DNA
<213> ORGANISM: Artificial
<220> FEATURE:
<223> OTHER INFORMATION: Synthesized primer

<400> SEQUENCE: 66
ggttccatgg gttttctttc cggtaa         26

<210> SEQ ID NO 67
<211> LENGTH: 37
<212> TYPE: DNA
<213> ORGANISM: Artificial
<220> FEATURE:
<223> OTHER INFORMATION: Synthesized primer

<400> SEQUENCE: 67
aaggatccga atactagtta tttcagttcg agttcgt         37

<210> SEQ ID NO 68
<211> LENGTH: 32

```
<212> TYPE: DNA
<213> ORGANISM: Artificial
<220> FEATURE:
<223> OTHER INFORMATION: Synthesized primer

<400> SEQUENCE: 68
aattccatgg cgaaacgtgc agtgattact gg                          32

<210> SEQ ID NO 69
<211> LENGTH: 39
<212> TYPE: DNA
<213> ORGANISM: Artificial
<220> FEATURE:
<223> OTHER INFORMATION: Synthesized primer

<400> SEQUENCE: 69
aaggatccga atactagtta atctttcagc ttgcgcatt                   39

<210> SEQ ID NO 70
<211> LENGTH: 26
<212> TYPE: DNA
<213> ORGANISM: Artificial
<220> FEATURE:
<223> OTHER INFORMATION: Synthesized primer

<400> SEQUENCE: 70
ggttccatgg tcattaaggc gcaaag                                 26

<210> SEQ ID NO 71
<211> LENGTH: 37
<212> TYPE: DNA
<213> ORGANISM: Artificial
<220> FEATURE:
<223> OTHER INFORMATION: Synthesized primer

<400> SEQUENCE: 71
gaggatccga atactagtta tcgcccctga atggcta                     37

<210> SEQ ID NO 72
<211> LENGTH: 70
<212> TYPE: DNA
<213> ORGANISM: Artificial
<220> FEATURE:
<223> OTHER INFORMATION: Synthesized primer

<400> SEQUENCE: 72
tatcatcaca agtggtcaga cctcctacaa gtaaggggct tttcgttatg tgtgtaggct    60
ggagctgctt                                                          70

<210> SEQ ID NO 73
<211> LENGTH: 70
<212> TYPE: DNA
<213> ORGANISM: Artificial
<220> FEATURE:
<223> OTHER INFORMATION: Synthesized primer

<400> SEQUENCE: 73
aaacggagcc tttcggctcc gttattcatt tacgcggctt caactttccg catatgaata    60
tcctccttag                                                          70

<210> SEQ ID NO 74
<211> LENGTH: 70
<212> TYPE: DNA
<213> ORGANISM: Artificial
<220> FEATURE:
```

<223> OTHER INFORMATION: Synthesized primer

<400> SEQUENCE: 74
catttggggt tgcgatgacg acgaacacgc attttagagg tgaagaattg tgtgtaggct    60
ggagctgctt                                                          70

<210> SEQ ID NO 75
<211> LENGTH: 70
<212> TYPE: DNA
<213> ORGANISM: Artificial
<220> FEATURE:
<223> OTHER INFORMATION: Synthesized primer

<400> SEQUENCE: 75
taaccggcgt ctgacgactg acttaacact caggctttat tgtccacttt catatgaata    60
tcctccttag                                                          70

<210> SEQ ID NO 76
<211> LENGTH: 1020
<212> TYPE: DNA
<213> ORGANISM: Artificial
<220> FEATURE:
<223> OTHER INFORMATION: Synthesized sequence for yjgB from Escherichia coli

<400> SEQUENCE: 76
atgtcgatga taaaaagcta tgccgcaaaa gaagcgggcg gagaactgga agtttatgag    60
tacgatcccg gtgagctgag gccacaagat gttgaagtgc aggtggatta ctgcgggatc   120
tgccattccg atctgtcgat gatcgataac gaatggggat tttcacaata tccgctggtt   180
gccgggcatg aggtgattgg gcgcgtggtg gcactcggga gcgccgcgca ggataaaggt   240
ttgcaggtcg tcagcgtgt cgggattggc tggacgcgc gtagctgtgg tcactgcgac   300
gcctgtatta gcggtaatca gatcaactgc gagcaaggtg cggtgccgac gattatgaat   360
cgcggtggct tgccgagaa gttgcgtgcg actggcaat gggtgattcc actgccagaa   420
aatattgata tcgagtccgc cgggccgctg ttgtgcggcg tatcacggt ctttaaacca   480 ctgttgatgc accatatcac tgctaccagc cgcgttgggg taattggtat tggcgggctg   540
gggcatatcg ctataaaaact tctgcacgca atgggatgcg aggtgacagc ctttagttct   600
aatccggcga agagcagga agtgctggcg atgggtgccg ataaagtggt gaatagccgc   660
gatccgcagg cactgaaagc actggcgggg cagtttgatc tcattatcaa caccgtcaac   720
gtcagcctcg actggcagcc ctattttgag gcgctgacct atggcggtaa tttccatacg   780
gtcggtgcgg ttctcacgcc gctgtctgtt ccggccttta cgttaattgc gggcgatcgc   840
agcgtctctg gttctgctac cggcacgcct tatgagctgc gtaagctgat gcgttttgcc   900
gcccgcagca aggttgcgcc gaccaccgaa ctgttcccga tgtcgaaaat taacgacgcc   960
atccagcatg tgcgcgacgg taaggcgcgt taccgcgtgg tgttgaaagc cgattattga  1020

<210> SEQ ID NO 77
<211> LENGTH: 552
<212> TYPE: DNA
<213> ORGANISM: Artificial
<220> FEATURE:
<223> OTHER INFORMATION: Synthesized sequence for thioesterase

<400> SEQUENCE: 77
atggcggaca cgttattgat tctgggtgat agcctgagcg ccgggtatcg aatgtctgcc    60
agcgcggcct ggcctgcctt gttgaatgat aagtggcaga gtaaaacgtc ggtagttaat   120

```
gccagcatca gcggcgacac ctcgcaacaa ggactggcgc gccttccggc tctgctgaaa      180
cagcatcagc cgcgttgggt gctggttgaa ctgggcggca atgacggttt gcgtggtttt      240
cagccacagc aaaccgagca aacgctgcgc cagattttgc aggatgtcaa agccgccaac      300
gctgaaccat tgttaatgca aatacgtctg cctgcaaact atggtcgccg ttataatgaa      360
gcctttagcg ccatttaccc caaactcgcc aaagagtttg atgttccgct gctgcccttt      420
tttatggaag aggtctacct caagccacaa tggatgcagg atgacggtat tcatcccaac      480
cgcgacgccc agccgtttat tgccgactgg atggcgaagc agttgcagcc tttagtaaat      540
catgactcat aa                                                         552
```

GENES AND USES THEREOF, METHODS FOR SYNTHESIZING ODD NUMBERED MEDIUM CHAIN ALIPHATIC ALDEHYDES AND METHODS FOR SYNTHESIZING EVEN NUMBERED MEDIUM CHAIN ALIPHATIC HYDROCARBONS

CROSS REFERENCE TO RELATED APPLICATONS

This application is the U.S. National Phase Application of International Application No. PCT/CN2015/089232, titled "GENES AND USES THEREOF, METHODS FOR SYNTHESIZING ODD NUMBER MEDIUM CHAIN ALIPHATIC ALDEHYDES AND METHODS FOR SYNTHSIZING EVEN NUMBERD MEDIUM CHAIN ALIPHATIC HYDROCARBIONS," filed on Sep. 9, 2015, which claims the priority to China Patent Application No. 201410566258.8, filed with the Patent Office of China on Oct. 22, 2014, titled "GENES AND USES, GENE ELEMENTS, METHODS FOR SYNTHESIZING ODD NUMBERED MEDIUM CHAIN ALIPHATIC ALDEHYDES AND METHODS FOR SYNTHESIZING EVEN NUMBERED MEDIUM CHAIN ALIPHATIC HYDROCARBONS," the contents of which are incorporated herein by reference in its entirety.

FIELD OF THE INVENTION

The present invention relates to the field of biotechnology, particularly to genes, coded proteins and uses thereof, gene elements, methods for synthesizing odd numbered medium chain aliphatic aldehydes, and methods for synthesizing even numbered medium chain aliphatic hydrocarbons.

BACKGROUND OF THE INVENTION

Due to the amphiphilic properties of medium chain aliphatic alcohols, they have very important applications in the industry, which can be used in the fields of surfactants, medicines, cosmetics and energy sources, with a market value of 100-120 million US dollars. The aliphatic hydrocarbon molecules having a carbon chain length of 6-16 are the main components of aviation kerosene, with advantages of high calorific value, low vapor pressure, low freezing point, low hygroscopicity, etc. 50% of commercial fatty alcohols are extracted from plant seeds or animal fats, and the remaining fatty alcohols and all hydrocarbons are refined from petroleum. Neither method is capable of meeting the requirements of sustainable and environment-friendly production by the modern society. On the contrary, with the rapid development of synthetic biology, genetically engineered bacterial strains can specifically synthesize the required products using renewable energy resources sugar, xylan, glycerol or the like.

In engineered *E. coli*, aliphatic alcohols and hydrocarbons are mainly derivatively synthesized from the fatty acid synthesis pathway. Respectively, three molecules, aliphatic acyl-ACP/CoA and free fatty acid, can be used as synthetic precursors. Conversion of aliphatic acyl-ACP/CoA or fatty acids to aliphatic aldehydes in the synthesis of hydrocarbon alcohols is a critical step, followed by reduction of aliphatic aldehydes to aliphatic alcohols or by decarbonylation reactions to become hydrocarbons with one carbon less. Microbial synthesis of aliphatic alcohols/hydrocarbons using aliphatic acyl-ACP/CoA as precursors has been reported since 2010. However, the artificial synthesis system for synthesizing medium chain hydrocarbon alcohols using free fatty acids as substrate only appeared in two reports until 2013. Howard et al. over-expressed thioesterase from *Cinnamomum camphora* in *E. coli*, released free fatty acids of specific length from aliphatic acyl-ACP, and simultaneously expressed the fatty acid reductase (FAR) encoded by the genes of luxC, luxD, luxE from *Photorhabdus luminescens* and fatty aldehyde decarbonylase from *Nostoc punctiforme* PCC73102, thereby the free fatty acids were reduced to aliphatic aldehydes and subsequentially decarboxylated into hydrocarbon molecules with one carbon less, and a hydrocarbon synthesis system using free fatty acid as the substrate was constructed, which was able to synthesize a relatively controllable length. Akhtar et al. discovered that the carboxylic acid reductase (CAR) from *Mycobacterium marinum* was able to convert the free fatty acids having a chain length ranging from C6 to C18 to the corresponding aliphatic aldehydes. This enzyme can be combined with an aliphatic aldehyde reductase or an aliphatic aldehyde decarboxylase to produce an aliphatic alcohol having an even numbered chain length (C8-C16) and a hydrocarbon compound having an odd numbered chain length (C7-C15) in vitro. The *E. coli* BL21 (DE3) strain is able to synthesize up to 350 mg/L of fatty alcohols with glucose as the carbon source in the minimum medium when such pathway is combined with a thioesterase capable of producing free fatty acid of a specific chain length in the cell.

Since the above two types of hydrocarbon synthesis systems using free fatty acids as the substrate both employed reductase for aldehyde reaction, they are called the reduction type hydrocarbon synthesis systems. Because under the same substrate conditions, the reductase requires the reducing power (NAD(P)H) and energy (ATP) provided by cells to perform reaction, while the reaction driving force of oxidase is provided by the oxygen molecules, oxidative synthesis system is a more economical microbial synthesis system. Currently, there has been no related work yet published on the artificially synthetic construction of oxidation-type hydrocarbons.

On the other hand, in the currently reported works, hydrocarbon alcohol artificial synthesis systems, whether taking aliphatic acyl-ACP/CoA or free fatty acid as the precursor, as the first step of the reduction reaction does not involve decarbonylation reaction, all the synthesized aliphatic alcohols are of even numbered carbon chains, while all the hydrocarbon molecules are of odd numbered carbon chains as a result of the one-step decarbonylation reaction. In fact, all the petroleum-based chemicals and fuels have diversity in structure, and simultaneously contain molecules of straight and branched chains, as well as odd and even numbered chains. An ideal biofuel should be both structurally and chemically similar to existing petroleum-based fuels. There has been work to alter the upstream fatty acid synthesis pathway for downstream synthesis of branched chain and even numbered chain alkanes. But there has been no work for directly regulating the downstream synthesis pathway.

SUMMARY OF THE INVENTION

In view of this, the present invention provides a gene, a coded protein and use thereof, a gene element, a method for synthesizing an odd numbered medium chain aliphatic aldehyde, and a method for synthesizing an even numbered medium chain aliphatic hydrocarbon. The process wherein α-dioxygenase converts the precursor fatty acid molecule to an important intermediate metabolite, aliphatic aldehyde, is an oxidation reaction, without requiring cells to provide additional reducing power and energy, thus reduces the burden of cell production; fills up the technical limitation that aliphatic alcohol product chain length is only even numbered, and that aliphatic hydrocarbon product chain length is mostly odd numbered, thereby can make bio-based bulk chemical and biofuel molecules more match with related petroleum-based products.

In order to achieve the above object of the invention, the present invention provides the following technical solutions.

The present invention provides a gene having:
(I) the nucleotide sequence set forth in SEQ ID No. 1; or
(II) a sequence complementary to the nucleotide sequence set forth in SEQ ID No. 1; or
(III) a sequence which encodes the same protein as that the nucleotide sequence of (I) or (II) does but differs from the nucleotide sequence of (I) or (II) due to genetic codon degeneracy; or
(IV) a sequence which is at least 80% homologous to the sequence of (I) or (II) or (III).

The present invention also provides use of the above gene for the synthesis of an aliphatic aldehyde, an odd numbered medium chain fatty acid, an odd numbered medium chain aliphatic alcohol, and an even numbered medium chain aliphatic hydrocarbon.

In some embodiments of the present invention, the aliphatic aldehyde is an odd numbered medium chain aliphatic aldehyde. The medium chain fatty acid, the medium chain aliphatic alcohol and the medium chain aliphatic hydrocarbon in the present invention represent a fatty acid, an aliphatic alcohol and an aliphatic hydrocarbon molecule comprising 8 to 14 carbon atoms, respectively.

In some embodiments of the present invention, the aliphatic aldehyde is an odd numbered medium chain aliphatic aldehyde.

In some embodiments of the present invention, the aliphatic aldehyde is 1-undecanal, tridecanal or pentadecenal.

In some embodiments of the present invention, the odd numbered medium chain aliphatic alcohol is 1-undecanol, 1-tridecanol or 1-pentadecanol.

In some embodiments of the present invention, the even numbered medium chain aliphatic hydrocarbon is aliphatic hydrocarbon having a chain length of C12 and C14.

The present invention also provides a vector comprising the gene (α-dox) set forth in SEQ ID NO: 1.

The present invention also provides a host cell comprising the vector described above.

In some embodiments of the present invention, the host cell is E. coli.

The present invention also provides a gene element for synthesizing an aliphatic aldehyde, which comprises the gene (α-dox) set forth in SEQ ID NO: 1.

The present invention also provides a gene element for synthesizing an odd numbered medium chain aliphatic aldehyde, which comprises the gene (α-dox) set forth in SEQ ID NO: 1 and a thioesterase gene.

The gene element provided in the present invention for synthesizing an odd numbered medium chain aliphatic aldehyde is pACYC-(T7-Dox-tesA') plasmid (numbered in the present invention as YX135), pACYC-(T7-Dox-BTE) plasmid (numbered in the present invention as YX104), and pACYC-(T7-Dox-BnFatA) plasmid (numbered in the present invention as YX105).

The present invention also provides a method for the construction of a gene element for synthesizing an odd numbered medium chain aliphatic aldehyde, comprising:

1) ligating the thioesterase gene (tesA') endogenous to E. coli into the pTrcHis2A vector to form a pHisTrc-tesA plasmid;
2) ligating the thioesterase sequence containing $P_{Trc}$ promoter into pACYCDuet-1 plasmid to form a pACYC-Trc-tesA plasmid;
3) ligating the α-dioxygenase gene (α-dox) set forth in SEQ ID NO: 1 into the pET21a plasmid to form a pET21a-Dox plasmid;
4) taking the pACYC-Trc-tesA as the vector, restriction-digesting with SpeI and BamHI, and purifying;
using 21A-Dox as the fragment template, restriction-digesting the pET21a-Dox plasmid with XbaI and BamHI, gel-extracting, and ligating to the vector to construct a pACYC-Trc-tesA-Dox (CYX134) plasmid.

The present invention also provides a gene element for synthesizing an aliphatic alcohol, which comprises the gene (α-dox) set forth in SEQ ID NO: 1.

The present invention also provides a gene element for synthesizing an odd numbered medium chain aliphatic alcohol, which comprises the α-dioxygenase gene (α-dox) set forth in SEQ ID NO: 1, a thioesterase gene and an aldehyde reductase gene.

In some embodiments of the present invention, the aldehyde reductase gene is selected from the group consisting of a gene having the nucleotide sequence set forth in SEQ ID No. 2, adhP, yjgB, yqhD or adhE.

The gene element provided in the present invention for synthesizing an odd numbered medium chain aliphatic alcohol is pACYC-Trc-tesA-Dox plasmid (numbered in the present invention as CYX134), pACYC-(T7-Dox)-(T7-tesA') plasmid (numbered in the present invention as YX220), pACYC-(T5-Dox)-(T7-tesA') plasmid (numbered in the present invention as YX232), pACYC-(Trc-Dox)-(T7-tesA') plasmid (numbered in the present invention as YX233), pACYC-(LacUV5-Dox)-(T7-tesA') plasmid (numbered in the present invention as YX234), pACYC-(BAD-Dox)-(T7-tesA') plasmid (numbered in the present invention as YX235), pACYC-(T7-Doxhis)-(T7-tesA') plasmid (numbered in the present invention as YX221), pACYC-(T5-Doxhis)-(T7-tesA') plasmid (numbered in the present invention as YX222), pACYC-(Trc-Doxhis)-(T7-tesA') plasmid (numbered in the present invention as YX223), pACYC-(LacUV5-Doxhis)-(T7-tesA') plasmid (numbered in the present invention as YX224), pACYC-(BAD-Doxhis)-(T7-tesA') plasmid (numbered in the present invention as YX225), pACYC-(T7-Dox-tesA') plasmid (numbered in the present invention as YX135), pACYC-(T5-Dox-tesA') plasmid (numbered in the present invention as YX136), pACYC-(LacUV5-Dox-tesA') plasmid (numbered in the present invention as YX137), pACYC-(Trc-Dox-tesA') plasmid (numbered in the present invention as YX138), pBAD33-Dox-tesA' plasmid (numbered in the present invention as YX140), pACYC-(T7-tesA'-Dox) (numbered in the present invention as YX131), pACYC-(T5-tesA'-Dox) plasmid (numbered in the present invention as YX132), pACYC-(LacUV5-tesA'-Dox) plasmid (numbered in the present invention as YX133), pACYC-(Trc-tesA'-Dox) plasmid (numbered in the present invention as YX134), pBAD33-tesA'-Dox plasmid (numbered in the present invention as YX130), pACYC-(T7-Dox-BTE) plasmid (numbered in the present invention as YX104), pACYC-(T7-Dox-BnFatA) plasmid (numbered in the present invention as YX105), pACYC-(Trc-tesA'-Dox-AdhP) plasmid (numbered in the present invention as CYX143), pACYC-(Trc-tesA'-Dox-yjgB) plasmid (numbered in the present invention as CYX144), pACYC-(Trc-tesA'-Dox-yqhD)

plasmid (numbered in the present invention as CYX145), pACYC-(Trc-tesA'-Dox-AdhE) plasmid (numbered in the present invention as CYX146), and pACYC-(Trc-tesA'-Dox-slr1192) plasmid (numbered in the present invention as CYX147).

A method for the construction of a gene element for synthesizing an odd numbered medium chain aliphatic alcohol, characterized in ligating different types or sources of aldehyde dehydrogenase genes (adhP, yjgB, yqhD, adhE and slr1192 set forth in SEQ ID NO: 2) into the pET28a plasmid to form 28a-AdhP, 28a-YjgB, pET28a-YqhD, pET28a-AdhE, pET28a-Slr1192 plasmids.

Taking CYX134 (pACYC-Trc-tesA-Dox) as the vector, restriction-digesting with SpeI and BamHI, and purifying. Respectively taking 28a-AdhP, 28a-YjgB, pET28a-YqhD, PET28a-AdhE and pET28a-Slr1192 as the template, restriction-digesting with SpeI and BamHI, Gel-extracting, and ligating to the vector.

The present invention also provides a gene element for synthesizing an even numbered medium chain aliphatic hydrocarbon, which comprises the gene according to claim 1, a thioesterase gene and an aldehyde decarbonylase gene.

In some embodiments of the present invention, the aldehyde decarbonylase gene is selected from the group consisting of a gene having the nucleotide sequence set forth in SEQ ID No. 3, 4 or 5 or ad73102.

The gene element provided in the present invention for synthesizing an even numbered medium chain aliphatic hydrocarbon is pACYC-(Trc-tesA'-Dox-CER1) plasmid (numbered in the present invention as CYX148), pACYC-(Trc-tesA'-Dox-AD9313) plasmid (numbered in the present invention as CYX149), pACYC-(Trc-tesA'-Dox-AD7942) plasmid (numbered in the present invention as CYX150), and pACYC-(Trc-tesA'-Dox-AD73102) plasmid (numbered in the present invention as CYX151).

The present invention also provides a method for the construction of a gene element for synthesizing an even numbered medium chain aliphatic hydrocarbon: ligating different types or sources of the aldehyde decarbonylase gene (cer1 set forth in SEQ ID NO:3, ad9313 set forth in SEQ ID NO:4, ad7942 set forth in SEQ ID NO:5, and ad73102) into the pET28a plasmid to form pET28a-CER1, PET28a-AD9313, pET28a-AD7942 and pET28a-AD73102 plasmids.

Respectively taking CYX134 as the vector. Taking pET28a-CER1, pET28a-AD9313, pET28a-AD7942 and pET28a-AD73102 as the template, restriction-digesting, gel-extracting, and ligating to the vector.

The present invention provides a method for synthesizing an odd numbered medium chain aliphatic aldehyde, comprising the steps of:
  step 1: ligating the gene described above into a vector to construct an expression vector;
  step 2: transforming a host cell with the expression vector, expressing and collecting the expression product.
  Specifically, comprising the steps of:
  1) ligating the α-dioxygenase gene into the pACYC-Trc-tesA plasmid from the dox gene with the RBS in pET21a-Dox plasmid to form a CYX134 plasmid;
  2) transforming the CYX134 plasmid into E. coli BL21 (DE3) strain, fermenting, and collecting the product.

The present invention also provides a method for synthesizing an odd numbered medium chain aliphatic alcohol, comprising the steps of:
  step 1: constructing a first vector comprising a thioesterase gene and a promoter for the thioesterase gene;
  step 2: ligating the gene described above into the first vector by restriction-digesting to construct a second vector;
  step 3: ligating an aldehyde reductase gene into the second vector by restriction-digesting to construct an expression vector;
  step 4: transforming a host cell with the expression vector, expressing and collecting the expression product.
  Specifically, comprising the steps of:
  1) restriction-digesting aldehyde reductase genes of different sources from the plasmids of 28a-AdhP, 28a-YjgB, pET28a-YqhD, pET28a-AdhE and pET28a-Slr1192 with XbaI and BamHI, then respectively ligating into CYX134 plasmids restriction-digested with SpeI and BamHI, to form CYX143, CYX144, CYX145, CYX146 and CYX147 plasmids.

Transforming each plasmid into E. coli BL21 (DE3) strain, fermenting, and collecting the product.

The present invention also provides a method for synthesizing an even numbered medium chain aliphatic hydrocarbon, comprising the steps of:
  step 1: constructing a first vector comprising a thioesterase gene and a promoter for the thioesterase gene;
  step 2: ligating the gene according to claim 1 into the first vector by restriction-digesting to construct a second vector;
  step 3: ligating an aldehyde decarbonylase gene into the second vector by restriction-digesting to construct an expression vector;
  step 4: transforming a host cell with the expression vector, expressing and collecting the expression product.
  Specifically, comprising the steps of:
  1) respectively ligating aldehyde decarbonylase genes of different sources into CYX134 plasmid from the plasmids of pET28a-CER1, pET28a-AD9313, pET28a-AD7942 and pET28a-AD73102, to form CYX148, CYX149, CYX150 and CYX151 plasmids.
  2) transforming each plasmid into E. coli BL21 (DE3) strain, fermenting, and collecting the product.

The present invention provides a method for synthesizing an odd number medium chain aliphatic alcohol by fed-batch fermentation: transforming the CYX144 plasmid and FadR plasmid a into host cell by heat shock, and performing fed-batch fermentation.

The CYX144 plasmid is pACYC-(Trc-tesA'-Dox-yjgB).
The FadR plasmid is pTrcHis2A-fadR.

Specifically, the present invention provides a method for synthesizing an odd number medium chain aliphatic alcohol by fed-batch fermentation: transforming the CYX144 and FadR plasmids into E. coli BL21 (DE3) strain by heat shock, and cultivating overnight on LB solid plates at 30° C., picking single colonies of the recon are inoculating in 2 mL of LB medium at 30° C. until OD is 2.5-4, and transferring and inoculating in 20 mL of M9 medium at a ratio of 1:100, cultivating at 30° C. until OD is 2.5-4, and further transferring and inoculating in 800 mL of M9 medium at a ratio of 1:100. When OD rises to 2.5-4, centrifugally concentrating the culture solution to 50 mL, and inoculating into 2.5 L fermenter for fed-batch fermentation. When OD rises to 15, inducing with 10 μM IPTG. Sampling every 4 h, and taking 15 mL every time for analysis of cell density, and glycerol, acetic acid, fatty alcohol concentrations. The content of each antibiotic in the solid and liquid mediais chloramphenicol 34 μg/mL and ampicillin 100 μg/mL.

The cell density is measured at a wavelength of 600 using a TU-1810 UV-Vis spectrophotometer (Beijing Purkinje General Instrument Co., Ltd.).

Measurement of glycerol and acetic acid concentration: taking 1 mL fermentation broth and centrifuging at 12,000 rpm for 10 min, taking the supernatant and filtering through a 0.22 μm filtration membrane, diluting as appropriate, or directly injecting into HPLC for separation and detection. HPLC is Waters e2695, the detector is 2414 RI differential detector, and the chromatographic column is Aminex HPX-87H column (BioRad, CA); the column temperature is maintained at 65° C., and the mobile phase is 5 mM dilute sulphuric acid aqueous solution with a flow rate of 0.6 mL/min.

Extraction of aliphatic alcohol.

Detection of aliphatic alcohol extraction samples.

As shown in FIG. 7, after 18.5 h of induction, the yield of aliphatic alcohol reaches 1.95 g/L, the OD value reaches 124.5 and the productivity is 0.105 g/L/h. The rates of glycerol consumption and glycerol addition are almost the same during the fermentation, without generation of acetic acid. During the process of fermentation, the proportion of aliphatic alcohols with different chain length is almost constant over time, and at the end of fermentation, the proportions of C11, C13 and C15 fatty alcohols are 18.6%, 66.2% and 15.2%, respectively.

The present invention provides a gene, having:
(I) the nucleotide sequence set forth in SEQ ID No. 1; or
(II) a sequence complementary to the nucleotide sequence set forth in SEQ ID No. 1; or
(III) a sequence which encodes the same protein as that the nucleotide sequence of (I) or (II) does but differs from the nucleotide sequence of (I) or (II) due to genetic codon degeneracy; or
(IV) a sequence which is at least 80% homologous to the sequence of (I) or (II) or (III).

Compared with the existing microbial synthesis pathway of aliphatic alcohol and aliphatic hydrocarbon, the present invention has the following two advantages: (1) the process wherein α-dioxygenase converts the precursor fatty acid molecule to an important intermediate metabolite, aliphatic aldehyde, is an oxidation reaction, without requiring the cells to provide additional reducing power and energy, thus reduces the burden of cell production; (2) it fills up the technical limitation that aliphatic alcohol product chain length is only even numbered, and that aliphatic hydrocarbon product chain length is mostly odd numbered, thereby can make bio-based bulk chemical and biofuel molecules more match with petroleum-based products.

The invention provides a microbial synthesis pathway and a construction method of the odd numbered medium chain aliphatic alcohol and the even numbered medium chain hydrocarbon by synthetic biological means; the present invention also provides an engineered *E. coli* that prepares odd numbered medium chain aliphatic alcohols and even numbered medium chain hydrocarbons using the above-described pathway.

DESCRIPTION OF THE DRAWINGS

(FIG. 1C) $C_{11}$ aldehyde mass spectrum; (FIG. 1D) $C_{11}$ alcohol mass spectrum; (FIG. 1E) $C_{13}$ aldehyde mass spectrum; (FIG. 1F) $C_{13}$ alcohol spectrum; (FIG. 1G) $C_{15:1}$ aldehyde mass spectrum; (FIG. 1H) $C_{15}$ alcohol mass spectrum; the numbers in parentheses are (match factor, reverse match factor); match factors and reverse match factors are capable of quantitatively describing the matching degree between product mass spectrum and database spectrum. If the value is higher than 900, it shows a very excellent match, 800-900 is an excellent match and 700-800 is a good match.

(FIG. 3A) comparison of the yield of aliphatic hydrocarbons of different engineering strains; (FIG. 3B) gas chromatogram of the product after induced fermentation at 30° C. for 40 h in *E. coli* BL21 (DE3) containing CYX148 plasmid; (FIG. 3C) gas chromatogram of the product after induced fermentation at 30° C. for 40 h in *E. coli* BL21 (DE3) containing CYX151 plasmid. 8: $C_{12}$ hydrocarbon; 9: $C_{14}$ hydrocarbon; (FIG. 3D) $C_{12}$ hydrocarbon mass spectrum; (FIG. 3E) $C_{14}$ hydrocarbon mass spectrum.

FIG. 5A shows the proportion results of the output of fatty acids of different chain length after induced fermentation at 30° C. for 40 h in *E. coli* BL21 (DE3) containing YX101, YX102 and YX103 plasmids in Example 8; FIG. 5B shows the proportion results of the output of aliphatic aldehydes and aliphatic alcohols of different chain length after induced fermentation at 30° C. for 40 h in *E. coli* BL21 (DE3) containing YX135, YX104 and YX105 plasmids in Example 8; FIG. 5C shows the results of the output of fatty acids after induced fermentation at 30° C. for 40 h in *E. coli* BL21 (DE3) containing YX101, YX102 and YX103 plasmids in Example 8; FIG. 5D shows the results of the output of aliphatic aldehydes and aliphatic alcohols after induced fermentation at 30° C. for 40 h in *E. coli* BL21 (DE3) containing YX135, YX104 and YX105 plasmids in Example 8.

FIG. 7A shows the curves of biomass (OD600), residual glycerol, acetic acid content, aliphatic alcohol content over time in fed-batch fermentation in Example 10; FIG. 7B shows the proportion of aliphatic alcohol content of different chain length in the fermentation broth after 9 hours, 17 hours and 27.5 hours of fed-batch fermentation in Example 10.

DETAILED DESCRIPTION OF THE INVENTION

Figure 1:
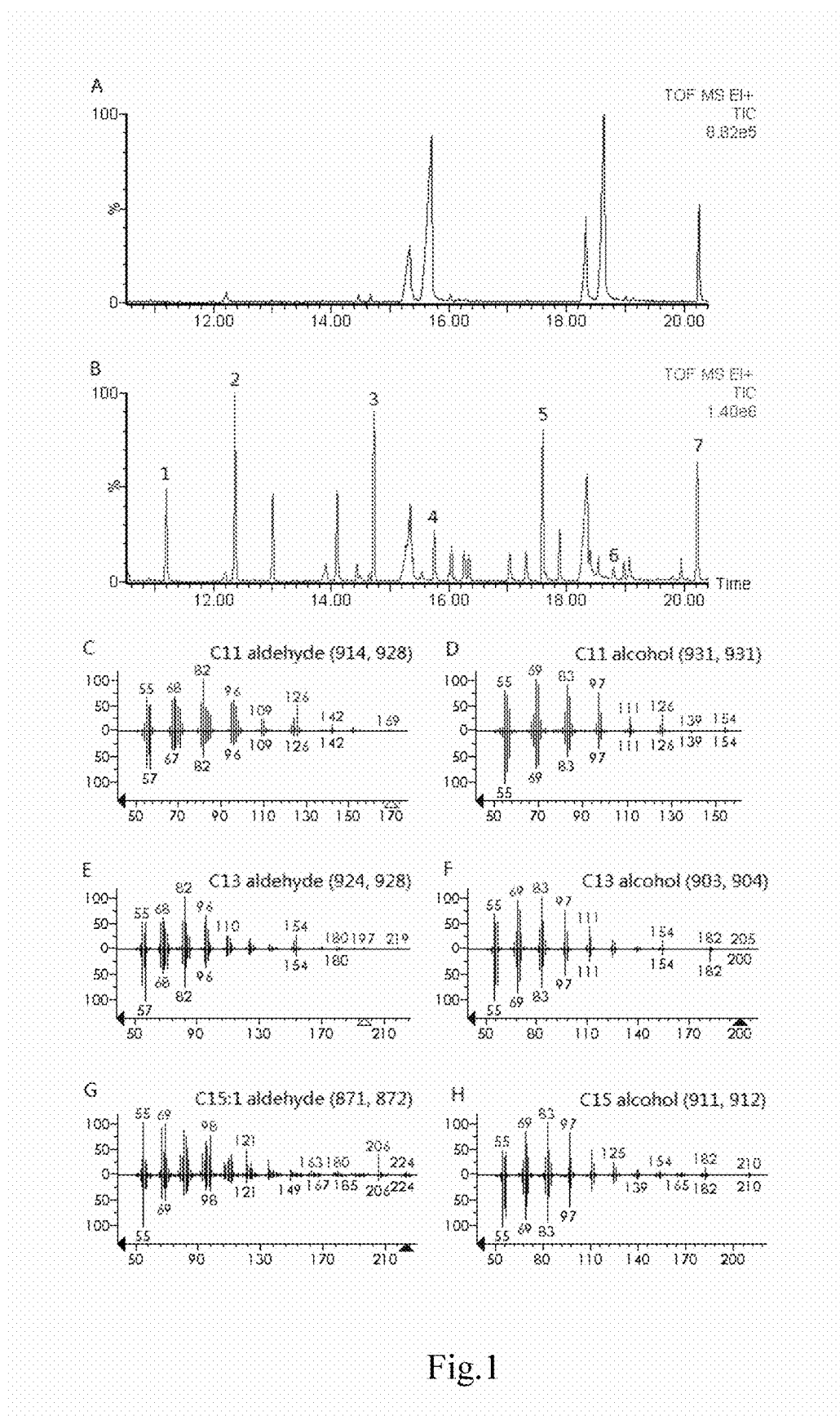
FIG. 1 shows the gas chromatogram of the product after induced fermentation at 30° C. for 40 h in *E. coli* BL21 (DE3) containing pACYC-Trc-tesA (FIG. 1A) or CYX134 plasmid (FIG. 1B) in Example 4; wherein, 1: $C_{11}$ aldehyde; 2: $C_{11}$ alcohol; 3: $C_{13}$ aldehyde; 4: $C_{13}$ alcohol; 5: $C_{15:1}$ aldehyde; 6: $C_{15}$ alcohol; 7: $C_{16}$ alcohol (internal standard, IS)

The present invention discloses a gene, a coded protein and use thereof, a gene element, methods for synthesizing an odd numbered medium chain aliphatic aldehyde, for synthesizing an odd numbered medium chain aliphatic alcohol and for synthesizing an even numbered medium chain aliphatic hydrocarbon. Those skilled in the art can use the content herein for reference and suitably modify the process parameters to achieve them. It should be noted that all similar alternatives and modifications will be apparent to those skilled in the art, and they are all deemed to be included in the method and use of the present invention. The method and use of the present invention have been described by way of preferred embodiments, and related personnel obviously can alter or appropriately change and combine the methods and uses described herein so as to realize and apply the technology of the present invention without departing from the content, spirit and scope of the present invention.

All the materials and reagents used in the gene, the encoded protein and use thereof, the gene element, the methods for the synthesis of an odd numbered medium chain aliphatic aldehyde, for the synthesis of an odd numbered medium chain aliphatic alcohol and for the synthesis of an even numbered medium chain aliphatic hydrocarbon, provided in the present invention are commercially available.

Plasmid No. and Information

| No. | Plasmid content |
|---|---|
| YX101 | pACYC-(T7-tesA') |
| YX 102 | pACYC-(T7-BTE) |
| YX 103 | pACYC-(T7-BnFatA) |
| YX 104 | pACYC-(T7-Dox-BTE) |
| YX 105 | pACYC-(T7-Dox-BnFatA) |
| YX 112 | pACYC-(Dox-tesA')-(T7-Dox) |
| YX 114 | pACYC-(Dox-tesA')-(T7-tesA') |
| YX 120 | pACYC-(T7-Dox) |
| YX 130 | pBAD33-tesA'-Dox |
| YX 131 | pACYC-(T7-tesA'-Dox) |
| YX 132 | pACYC-(T5-tesA'-Dox) |
| YX 133 | pACYC-(LacUV5-tesA'-Dox) |
| CYX 134 | pACYC-(Trc-tesA'-Dox) |
| YX 135 | pACYC-(T7-Dox-tesA') |
| YX 136 | pACYC-(T5-Dox-tesA') |
| YX 137 | pACYC-(LacUV5-Dox-tesA') |
| YX 138 | pACYC-(Trc-Dox-tesA') |
| YX 140 | pBAD33-Dox-tesA' |
| CYX 143 | pACYC-(Trc-tesA'-Dox-AdhP) |
| CYX 144 | pACYC-(Trc-tesA'-Dox-yjgB) |
| CYX 145 | pACYC-(Trc-tesA'-Dox-yqhD) |
| CYX 146 | pACYC-(Trc-tesA'-Dox-AdhE) |
| CYX 147 | pACYC-(Trc-tesA'-Dox-slr1192) |
| CYX 148 | pACYC-(Trc-tesA'-Dox-CER1) |
| CYX 149 | pACYC-(Trc-tesA'-Dox-AD9313) |
| CYX 150 | pACYC-(Trc-tesA'-Dox-AD7942) |
| CYX 151 | pACYC-(Trc-tesA'-Dox-AD73102) |
| YX 201 | pACYC-(T7-RFP) |
| YX 210 | pACYC-(T5-RFP) |
| YX 211 | pACYC-(LacUV5-RFP) |
| YX 212 | pACYC-(Trc-RFP) |
| YX 213 | pACYC-(BAD-RFP) |
| YX 221 | pACYC-(T7-Dox$_{his}$)-(T7-tesA') |
| YX 222 | pACYC-(T5-Dox$_{his}$)-(T7-tesA') |
| YX 223 | pACYC-(Trc-Dox$_{his}$)-(T7-tesA') |
| YX 224 | pACYC-(LacUV5-Dox$_{his}$)-(T7-tesA') |
| YX 225 | pACYC-(BAD-Dox$_{his}$)-(T7-tesA') |
| YX 220 | pACYC-(T7-Dox)-(T7-tesA') |
| YX 232 | pACYC-(T5-Dox)-(T7-tesA') |
| YX 233 | pACYC-(Trc-Dox)-(T7-tesA') |
| YX 234 | pACYC-(LacUV5-Dox)-(T7-tesA') |
| YX 235 | pACYC-(BAD-Dox)-(T7-tesA') |
| FabD | pTrcHis2A-fabD |
| FabG | pTrcHis2A-fabG |
| FabA | pTrcHis2A-fabA |
| FabI | pTrcHis2A-fabI |
| FabB | pTrcHis2A-fabB |
| FadR | pTrcHis2A-fadR |

Detailed Information of Plasmids

| Plasmid name | Replicon | Promoter and over-expressed gene | Resistance |
|---|---|---|---|
| YX101 | p15A | $P_{T7}$: tesA' (derived from E. coli MG1655) | Chloramphenicol |
| YX102 | p15A | $P_{T7}$: bte (derived from U. californica, optimized with E. coli codons) | Chloramphenicol |
| YX103 | p15A | $P_{T7}$: BnfatA (derived from B. napus, optimized with E. coli codons) | Chloramphenicol |
| YX104 | p15A | $P_{T7}$: dox and bte (dox is derived from O. sativa, optimized with E. coli codons) | Chloramphenicol |
| YX105 | p15A | $P_{T7}$: dox and BnfatA | Chloramphenicol |
| YX112 | p15A | $P_{T7}$: dox and tesA', $P_{T7}$: dox | Chloramphenicol |
| YX114 | p15A | $P_{T7}$: dox and tesA', $P_{T7}$: tesA' | Chloramphenicol |
| YX120 | p15A | $P_{Trc}$: tesA' | Chloramphenicol |
| YX130 | p15A | $P_{BAD}$: tesA' and dox | Chloramphenicol |
| YX131 | p15A | $P_{T7}$: tesA' and dox | Chloramphenicol |
| YX132 | p15A | $P_{T5}$: tesA' and dox | Chloramphenicol |
| YX133 | p15A | $P_{lacUV5}$: tesA' and dox | Chloramphenicol |
| CYX134 | p15A | $P_{Trc}$: tesA' and dox | Chloramphenicol |
| YX135 | p15A | $P_{T7}$: dox and tesA' | Chloramphenicol |
| YX136 | p15A | $P_{T5}$: dox and tesA' | Chloramphenicol |
| YX137 | p15A | $P_{lacUV5}$: dox and tesA' | Chloramphenicol |
| YX138 | p15A | $P_{Trc}$: dox and tesA' | Chloramphenicol |
| YX140 | p15A | $P_{BAD}$: dox and tesA' | Chloramphenicol |
| CYX143 | p15A | $P_{Trc}$: tesA', dox and adhP (adhP is derived from E. coli BL21(DE3))) | Chloramphenicol |
| CYX144 | p15A | $P_{Trc}$: tesA', dox and yjgB (yjgB is derived from E. coli BL21(DE3))) | Chloramphenicol |
| CYX145 | p15A | $P_{Trc}$: tesA', dox and yqhD (yqhD is derived from E. coli BL21(DE3), with NdeI restriction site removed) | Chloramphenicol |
| CYX146 | p15A | $P_{Trc}$: tesA', dox and adhE (yqhD is derived from E. coli BL21(DE3), with NcoI restriction site removed) | Chloramphenicol |
| CYX147 | p15A | $P_{Trc}$: tesA', dox and slr1192 (slr1192 is derived from Synechocystis sp. PCC 6803, optimized with E. coli codons) | Chloramphenicol |

-continued

| Plasmid name | Replicon | Promoter and over-expressed gene | Resistance |
| --- | --- | --- | --- |
| CYX148 | p15A | $P_{Trc}$: tesA', dox and cer1 (cer1 is derived from *A. thaliana*, optimized with *E. coli* codons) | Chloramphenicol |
| CYX149 | p15A | $P_{Trc}$: tesA', dox and ad9313 (ad9313 is derived from *P. marinus* MIT9313, optimized with *E. coli* codons) | Chloramphenicol |
| CYX150 | p15A | $P_{Trc}$: tesA', dox and ad7942 (ad7942 is derived from *S. elongates* PCC7942, optimized with *E. coli* codons) | Chloramphenicol |
| CYX151 | p15A | $P_{Trc}$: tesA', dox and ad73102 (ad73102 is derived from *N. punctiforme* PCC73102, optimized with *E. coli* codons) | Chloramphenicol |
| YX201 | p15A | $P_{T7}$: rfp (derived from standard biology brick, Massachusetts Institute of Technology, BBa_E1010 element) | |
| YX210 | p15A | $P_{T5}$: rfp | |
| YX211 | p15A | $P_{lacUV5}$: rfp | |
| YX212 | p15A | $P_{Trc}$: rfp | |
| YX213 | p15A | $P_{BAD}$: rfp | |
| YX221 | p15A | $P_{T7}$: dox with 6*His tag, $P_{T7}$: tesA' | Chloramphenicol |
| YX222 | p15A | $P_{T5}$: dox with 6*His tag, $P_{T7}$: tesA' | Chloramphenicol |
| YX223 | p15A | $P_{lacUV5}$: dox with 6*His tag, $P_{T7}$: tesA' | Chloramphenicol |
| YX224 | p15A | $P_{Trc}$: dox with 6*His tag, $P_{T7}$: tesA' | Chloramphenicol |
| YX225 | p15A | $P_{BAD}$: dox with 6*His tag, $P_{T7}$: tesA' | Chloramphenicol |
| YX220 | p15A | $P_{T7}$: dox, $P_{T7}$: tesA' | Chloramphenicol |
| YX232 | p15A | $P_{T5}$: dox, $P_{T7}$: tesA' | Chloramphenicol |
| YX233 | p15A | $P_{lacUV5}$: dox, $P_{T7}$: tesA' | Chloramphenicol |
| YX234 | p15A | $P_{Trc}$: dox, $P_{T7}$: tesA' | Chloramphenicol |
| YX235 | p15A | $P_{BAD}$: dox, $P_{T7}$: tesA' | Chloramphenicol |
| FabD | pBR322 | $P_{Trc}$: fabD (derived from *E. coli* MG1655, with XhoI restriction site removed) | Ampicillin |
| FabG | pBR322 | $P_{Trc}$: fabG (derived from *E. coli* MG1655, with NcoI restriction site removed) | Ampicillin |
| FabA | pBR322 | $P_{Trc}$: fabA (derived from *E. coli* MG1655) | Ampicillin |
| FabI | pBR322 | $P_{Trc}$: fabI (derived from *E. coli* MG1655) | Ampicillin |
| FabB | pBR322 | $P_{Trc}$: fabB (derived from *E. coli* MG1655) | Ampicillin |
| FadR | pBR322 | $P_{Trc}$: fabR (derived from *E. coli* MG1655) | Ampicillin |

The invention is further illustrated in conjunction with the following examples:

EXAMPLE 1

Construction of the Gene Element for Synthesizing an Odd Numbered Medium Chain Aliphatic Aldehyde Experiment Materials:

Thioesterase (TesA'): The thioesterase gene I (tesA') endogenous to *E. coli* was purchased from addgene (Plasmid 24636). The gene is placed into a plasmid having p15A as the replicon and placUV5 as the promoter, designated as pKS1, and the 75 bp nucleotide behind the start codon ATG is removed. The removed nucleotide encodes an amino acid sequence that is a signal peptide that is used to localize the enzyme in the intracellular substance. With this signal peptide sequence removed, the thioesterase can be enriched within the cells, and plenty of free fatty acids were produced in *E. coli*.

α-Dioxygenase (Dox): the protein sequence of α-dioxygenase (NCBI Reference Sequence: NP_001066718.1) reported in *Oryza sativa* is optimized according to the *E. coli* codons. The DNA molecule encoding the α-dioxygenase after optimization has the nucleotide sequence set forth in SEQ ID NO: 1, wherein the gene is synthesized in Genewiz.

Plasmid pTrcHis2A was purchased from Invitrogen.
Plasmid pACYCDuet-1 was purchased from Novagen.
Plasmid pET21a was purchased from Novagen.

Experiment Methods:

1. Construction of pHisTrc-tesA plasmid
   1) The vector was pTrcHis2A, restriction-digested with NcoI and BamHI; with a length of 4400; purified;
   2) The template was pKS1, amplified with the primers NcoI-tesA-fwd and BamHI-SpeI-tesA-rev; with a length of 575; gel-extracted, restriction-digested with NcoI and BamHI, purified and ligated to vector;
   3) Colony PCR with primer pTrcHis2A-F and primer pTrcHis2A-R, with the correct length of 894.

2. Construction of pACYC-Trc-tesA plasmid
   1) The pACYCDuet-1 was amplified with the primers AflII-pACYC-fwd and PstI-pACYC-rev, and with a length of 3810; gel-extracted, restriction-digested with PstI and AflII, and purified.
   2) The fragment template was pHisTrc-tesA; PCR was carried out with PstI-Gibson-pHisTrc-fwd and AflII-Gibson-rrnBT1-rev, with a length of 1190, gel-extracted, and Gibson ligated to vector.
   3) Colony PCR with Duet-seq-F and pACYCDuet-R, with a length of 1443.

3. Construction of pET21a-Dox plasmid
   1) The vector was pET21a, restriction-digested with NdeI and BamHI, with a length of 5350.
   2) The fragment template was the synthetic dox gene, amplified with the primers NdeI-Dox-fwd and BamHI-SpeI-Dox-rev, with a length of 1885, gel-extracted, restriction-digested with NdeI and BamHI, purified and ligated to vector.
   3) Colony PCR with the primer pET-fwd and primer pET-rev, with the correct length of 2401.

4. Construction of pET28a-Dox plasmid
1) The vector was pET28a, restriction-digested with NdeI and BamHI.
2) The fragment template was the synthetic dox gene, amplified with the primers NdeI-Dox-fwd and BamHI-SpeI-Dox-rev, with a length of 1885, gel-extracted, restriction-digested with NdeI and BamHI, purified and ligated to vector.
3) Colony PCR with the primer pET-fwd and the primer pET-rev.

5. Construction of pET21a-tesA plasmid
1) The vector was pET21a, restriction-digested with NdeI and BamHI.
2) The fragment template was pKS1, amplified with the primers NdeI-teaA-fwd and BamHI-SpeI-tesA-rev, gel-extracted, restriction-digested with NdeI and BamHI, purified and ligated to vector.
3) Colony PCR with the primer pET-fwd and the primer pET-rev.

EXAMPLE 2

Construction of the Gene Elements for Synthesizing Odd Numbered Medium Chain Aliphatic Alcohols Experiment Materials AdhE: Acetaldehyde coenzyme A reductase/ferric ion-dependent ethanol dehydrogenase, derived from the genome of *E. coli* BL21 (DE3) (NCBI-GeneID: 8180074), wherein the NcoI restriction site in the sequence was substituted by single point mutation.

AdhP: Ethanol active dehydrogenase/acetaldehyde active reductase, derived from the genome of *E. coli* BL21 (DE3) (NCBI-GeneID: 8181169).

YqdD: NADPH-dependent acetaldehyde reductase, derived from the genome of *E. coli* BL21 (DE3) (NCBI-GeneID: 8180496), wherein the NdeI restriction site in the sequence was substituted by single point mutation.

TABLE 1

The list of primers needed in the construction of the gene elements for synthesizing odd numbered medium chain aliphatic aldehydes

| Primer name | Sequence No. | Sequence |
| --- | --- | --- |
| NcoI-tesA-fwd | SEQ ID No. 6 | CCTCCATGGCGGACACGTTATTGATTCTG |
| BamHI-SpeI-tesA-rev | SEQ ID No. 7 | CCGGGATCCGAATACTAGTTATGAGTCATGATTTACTA |
| pTrcHis2A-F | SEQ ID No. 8 | ACAGCGCCGCTGAGAAAAAGCGAA |
| pTrcHis2A-R | SEQ ID No. 9 | AGTTCGGCATGGGGTCAGGT |
| AflII-pACYC-fwd | SEQ ID No. 10 | GGCCCTTAAGTCGAACAGAAAGTA |
| PstI-pACYC-rev | SEQ ID No. 11 | TATCTGCAGCATAAGGGAGAGCGTCGAGA |
| PstI-Gibson-pHisTrc-fwd | SEQ ID No.12 | TCTCGACGCTCTCCCTTATGCTGCAGACATCATAACGGTTCTGGCA |
| AflII-Gibson-rrnBT1-rev | SEQ ID No. 13 | TACGATTACTTTCTGTTCGACTTAAGGGCGGATTTGTCCTACTCAG |
| Duet-seq-F | SEQ ID No. 14 | GTCCATGTGCTGGCGTTCAA |
| pACYCDuet-R | SEQ ID No15 | GATTATGCGGCCGTGTACAA |
| NdeI-Dox-fwd | SEQ ID No. 16 | ACAGGCATATGGGCAGCGGTTTATTCAA |
| BamHI-SpeI-Dox-rev | SEQ ID No. 17 | GGGGGATCCGAATACTAGTTATTAATAGTCTGCATCCC |
| pET-fwd | SEQ ID No. 18 | TCTTCCCCATCGGTGATGTC |
| pET-rev | SEQ ID No. 19 | TCACGCTGCGCGTAACCACCACA |

YjgB: Ethanol dehydrogenase (atypical zinc ethanol dehydrogenase-like protein, zinc and NADPH-dependent), derived from the genome of E. coli BL21 (DE3) (NCBI-GeneID: 8182107).

Slr1192: Ethanol dehydrogenase containing zinc, derived from Synechocystis sp. PCC 6803, with the protein sequence of NCBI Reference Sequence: NP_443028.1, optimized according to E. coli codons; after optimization, the DNA molecule encoding Slr1192 has the nucleotide sequence set forth in SEQ ID NO: 2, and the gene was synthesized in our laboratory.

Plasmid pET28a was purchased from Novagen.

Experiment Methods

1. Construction of pHisTrc-tesA plasmid
1) The vector was pTrcHis2A, restriction-digested with NcoI and BamHI; with a length of 4400; purified.
2) The template was pKS1, amplified with the primers NcoI-tesA-fwd and BamHI-SpeI-tesA-rev; with a length of 575; gel-extracted, restriction-digested with NcoI and BamHI, purified and ligated to vector.
3) Colony PCR with primer pTrcHis2A-F and primer pTrcHis2A-R, with the correct length of 894.

2. Construction of pACYC-Trc-tesA plasmid
1) The pACYCDuet-1 was amplified with the primers AflII-pACYC-fwd and PstI-pACYC-rev, and with a length of 3810; gel-extracted, restriction-digested with PstI and AflII, and purified.
2) The fragment template was pHisTrc-tesA; PCR was carried out with PstI-Gibson-pHisTrc-fwd and AflII-Gibson-rrnBT1-rev, with a length of 1190, gel-extracted, and Gibson ligated to vector.
3) Colony PCR with Duet-seq-F and pACYCDuet-R, with a length of 1443.

3. Construction of pET21a-Dox plasmid
1) The vector was pET21a, restriction-digested with NdeI and BamHI, with a length of 5350.
2) The fragment template was the synthetic dox gene, amplified with the primers NdeI-Dox-fwd and BamHI-SpeI-Dox-rev, with a length of 1885, gel-extracted, restriction-digested with NdeI and BamHI, purified and ligated to vector.
3) Colony PCR with the primer pET-fwd and primer pET-rev, with the correct length of 2401.

4. Construction of pET28a-AdhP plasmid
1) The vector was pET28a, restriction-digested with NdeI and BamHI, with a length of 5400.
2) The fragment template was E. coli BL21 (DE3) genome, amplified with primers NdeI-AdhP-fwd and BamHI-SpeI-AdhP-rev, with a length of 1036.
3) Colony PCR with primer pET-fwd and primer pET-rev, with the correct length of 1552.

5. Construction of plasmids pET28a-YjgB, pET28a-YqhD, pET28a-AdhE and pET28a-Slr1192
1) The vector was pET28a-AdhP, restriction-digested with NdeI and SpeI, gel-extracted for the fragments with a length of 5350.
2) The fragment template was E. coli BL21 (DE3) genome, amplified with primers NdeI- * -fwd and SpeI- * -rev for different gene fragments (*** represents a gene name), see primer sequence in Table 3, and the fragment name and length after PCR are shown in Table 2, wherein substitution of NdeI restriction site was required in YqhD and substitution of NcoI restriction site was required in AdhE, therefore it was needed to perform PCR amplification of two parts on the left and right sides with the mutation site as the center, with the fragments gel-extracted followed by overlapping, and finally the fragments with the NdeI and SpeI restriction sites were gel-extracted; restriction-digested with NdeI and SpeI, purified and ligated to vector.
3) Colony PCR with primer pET-fwd and primer pET-rev, with the correct length shown in Table 2.

TABLE 2

Detailed information of the fragments

| Fragment name | Fragment length | Colony PCR length |
|---|---|---|
| YjgB | 1038 | 1564 |
| YqhD-left | 808 | 1705 |
| YqhD-right | 392 | |
| YqhD | 1179 | |
| AdhE-left | 1981 | 3217 |
| AdhE-right | 731 | |
| AdhE | 2691 | |
| slr1192 | 1026 | 1552 |

TABLE 3

The list of primers needed in the construction of the gene elements for synthesizing odd numbered medium chain aliphatic alcohols

| Primer name | Sequence No. | Sequence |
|---|---|---|
| NdeI-AdhP-fwd | SEQ ID No. 20 | GGGGACATATGAAGGCTGCAGTTGTTAC |
| BamHI-SpeI-AdhP-rev | SEQ ID No. 21 | GAGGGATCCGAATACTAGTTAGTGACGGAAATCAATCA |
| NdeI-yjgB-fwd | SEQ ID No. 22 | GGGGCATATGTCGATGATAAAAAGCTATG |
| SpeI-yjgB-rev | SEQ ID No. 23 | GGGACTAGTTATCAATAATCGGCTTTCAAC |
| NdeI-yqhD-fwd | SEQ ID No. 24 | GGGGCATATGAACAACTTTAATCTGCA |
| yqhD-ΔNdeI-left-rev | SEQ ID No. 25 | TGCGTTGCCCAGTCCTGCG |

TABLE 3-continued

The list of primers needed in the construction of the gene elements for synthesizing odd numbered medium chain aliphatic alcohols

| Primer name | Sequence No. | Sequence |
|---|---|---|
| yqhD-ΔNdeI-right-fwd | SEQ ID No. 26 | CGCAGGACTGGGCAACGCACATGCTGGGCCAC GAACTGA |
| SpeI-yqhD-rev | SEQ ID No. 27 | GGGACTAGTTAGCGGGCGGCTTCGTATA |
| NdeI-adhE-fwd | SEQ ID No. 28 | GGTTCATATGGCTGTTACTAATGTCGC |
| adhE-ΔNcoI-left-rev | SEQ ID No. 29 | GCGTGAGTTACTGCGTCCAG |
| adhE-ΔNcoI-right-fwd | SEQ ID No. 30 | CTGGACGCAGTAACTCACGCGATGGAAGCTTA TGTTTCTGT |
| SpeI-adhE-rev | SEQ ID No. 31 | GGGACTAGTTAAGCGGATTTTTTCGCTTTTTC |
| NdeI-slr1192-fwd | SEQ ID No. 32 | GGTACATATGATCAAGGCTTACGCTGC |
| SpeI-slr1192-rev | SEQ ID No. 33 | GGGACTAGTTAGTTTTTAGAGTGAGACA |

EXAMPLE 3

Construction of the Gene Elements for Synthesizing Even Numbered Medium Chain Aliphatic Hydrocarbons Experiment Materials CER1: Aliphatic aldehyde decarbonylase, derived from *Arabidopsis thaliana*; the protein sequence was UniProtKB/Swiss-Prot: F4HVY0.1, optimized according to *E. coli* codons; after optimization, the DNA molecule encoding CER1 has the nucleotide sequence set forth in SEQ ID NO: 3, and the gene was synthesized in genscript.

AD9313: Aliphatic aldehyde decarbonylase, derived from *Prochlorococcus marinus* MIT9313; the protein sequence was NCBI Reference Sequence: NP_895059.1, optimized according to *E. coli* codons; after optimization, the DNA molecule encoding AD9313 has the nucleotide sequence set forth in SEQ ID NO: 4, and the gene was synthesized in our laboratory.

AD7942: Aliphatic aldehyde decarbonylase, derived from *Synechococcus elongatus* PCC7942; the protein sequence was accession number: YP_400610, optimized according to *E. coli* codons; after optimization, the DNA molecule encoding AD7942 has the nucleotide sequence set forth in SEQ ID NO: 5, and the gene was synthesized in GENEART.

AD73102: Aliphatic aldehyde decarbonylase, derived from *Nostoc punctiforme* PCC73102; the protein sequence was accession number: YP_001865325, optimized according to *E. coli* codons; the DNA molecule encoding AD73102 after optimization was a gift from Squire J. Booker's group of the Pennsylvania State University, USA.

Experiment Methods

Construction of plasmids pET28a-CER1, pET28a-AD9313, pET28a-AD7942 and pET28a-AD73102

1) The vector was pET28a-AdhP, restriction-digested with NdeI and SpeI, gel-extracted for the fragments with a length of 5350.
2) Amplified with primers NdeI- * -fwd and SpeI- * -rev for different gene fragments (*** represents a gene name), see primer sequence in Table 5, and the fragment name and length after PCR are shown in Table 4; gel-extracted, restriction-digested with NdeI and SpeI, purified and ligated to vector.
3) Colony PCR with primer pET-fwd and primer pET-rev, with the correct length shown in Table 4.

TABLE 4

Detailed information of the fragments

| Fragment name | Fragment length | Colony PCR length |
|---|---|---|
| CER1 | 1893 | 2419 |
| ADC9313 | 747 | 1273 |
| ADC7942 | 715 | 1240 |
| ADC73102 | 714 | 1240 |

TABLE 5

The list of primers needed in the construction of the gene elements for synthesizing even numbered medium chain aliphatic hydrocarbons

| Primer name | Sequence No. | Sequenc |
|---|---|---|
| NdeI-CER1-fwd | SEQ ID No. 34 | GTTTCATATGGCTACCAAACCGGGTGT |
| SpeI-CER1-rev | SEQ ID No. 35 | AATACTAGTTAGTGGTGCGGCAGGAGCA |

TABLE 5-continued

The list of primers needed in the construction of the gene elements for synthesizing even numbered medium chain aliphatic hydrocarbons

| Primer name | Sequence No. | Sequenc |
|---|---|---|
| NdeI-ADC9313-fwd | SEQ 1D No. 36 | TTTTCATATGCCGACCCTGGAAATGCC |
| SpeI-ADC9313-rev | SEQ 1D No. 37 | GGTACTAGTTAGCTAACCAGTGCTGCTGCT |
| NdeI-AD7942-fwd | SEQ ID No. 38 | ATATACATATGCCGCAGCTGGAAGCGAG |
| SpeI-AD7942-rev | SEQ ID No. 39 | AATACTAGTTATTACACCGCCGCCAGGC |
| NdeI-AD73102-fwd | SEQ ID No. 40 | AACCACATATGCAGCAGCTGACCGATCA |
| SpeI-AD73102-rev | SEQ ID No. 41 | GGGACTAGTTATGCACCAATCAGACCAT |

EXAMPLE 4

Verification of the Feasibility of α-Dioxygenase for Synthesizing Odd Numbered Medium Chain Aliphatic Alcohols and Even Numbered Medium Chain Aliphatic Hydrocarbons Experiment Methods:

1. Construction of pACYC-Trc-tesA-Dox (CYX134) plasmid
1) The vector was pACYC-Trc-tesA, restriction-digested with SpeI and BamHI, and purified.
2) The fragment template was 21A-Dox, restriction-digested with XbaI and BamHI, with a length of 1911, gel-extracted and ligated to vector.
2. Plasmid CYX134 was transformed into E. coli BL21 (DE3) strain by heat shock and screened on LB solid plate. The cells were all cultured in an incubator at 30° C., and the content of each antibiotic in the solid and liquid media was 34 µg/mL chloramphenicol.
3. The E. coli BL21 (DE3) strain transformed with the plasmid pACYC-Dox-tesA' was subjected to fermentation. The recombinant single colonies were inoculated in LB medium and cultured at 30° C. overnight, and inoculated in 5 mL of M9 medium at a ratio of 1:100 and subjected to fermentation on a shaker at 220 rpm at 30° C. When the biomass was between OD600=1.0-1.2, 1 mM IPTG was added, and after 40 h of induced expression, the aliphatic alcohol samples were extracted for detection.
4. Extraction of aliphatic alcohols, specifically:
1) 0.5 mL of medium fermented at 30° C. for 40 h after induction was sampled and 25 mg/L of cetyl alcohol was added as internal standard.
2) 0.5 mL of ethyl acetate was added, vortex-shaked for 5 min, and centrifuged at 15000 rpm for 2 min.
3) The top-layer organic phase was aspirated and filtered through a 0.22 µm nylon membrane. Samples were stored in a −80° C. refrigerator prior to injecting.
5. Detection of aliphatic alcohol extraction samples. The Gas Chromatography-Mass Spectrometer (GC/MS) system involved in this experiment was the Waters GCT Premier MICROMASS system, which included:
1) Agilent 7683 autosampler
2) Agilent 6890 Gas Chromatography (GC, Agilent Technologies, USA)
3) Time-of-Flight Mass Spectrometer (TOF-MS, Waters Corp., USA)
4) J & W DB-5 capillary quartz column (30 m length, I.D. 0.25 mm, Film 0.25 µm, Agilent Technologies, USA)

GC conditions were as follows: DB-5 gas chromatography column was employed, with a injecting volume of 1 µL; post-column shunt technology was employed, with the split ratio of 2:1. The inlet temperature was 260° C. and the GC interface temperature was 280° C. Taking high-purity helium as the carrier gas, with 91 Kpa constant pressure. The program of temperature rising of the chromatographic separation was as follows: the initial temperature was maintained at 70° C. for 2 min, then the temperature raised to 290° C. at a rate of 8° C.·min$^{-1}$, and kept at 290° C. for 6 min. TOF/MS.

Mass spectrometric conditions were as follows: the mass spectrometry ionization mode was positive ion mode electron Impact ionization (EI+), of which the ionization voltage was 70 eV, and the source temperature maintained at 250° C. The scanning range of mass spectrometry was 50-800 m/z and the scanning speed was 2 scan·s$^{-1}$.

Qualitative and quantitative analysis of the products: GC-TOF/MS data were qualitatively and quantitatively analyzed using Masslynx software (Version 4.1, Waters Corp., USA). The chromatography peaks were identified by NIST database (National Institute of Standard and Technology library, NIST, 2005, Gaithersburg, Md.) and the peak areas of metabolites were automatically integrated by QuanLynx software. The ratio of the peak area of the total ion chromatogram of each substance to the peak area of the internal standard on the same spectrum was used to obtain the normalized FAME and relative concentrations of hydrocarbons.

Experiment Results

Figure 2:
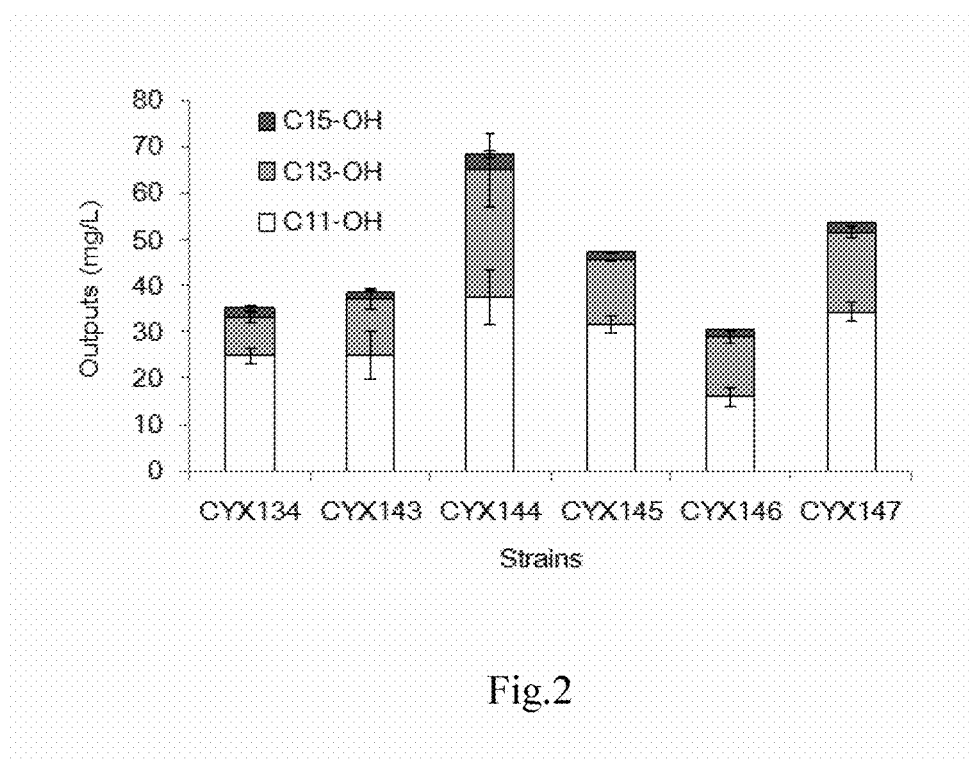
FIG. 2 shows the results of the aliphatic alcohol output after induced fermentation at 30° C. for 40 h in *E. coli* BL21 (DE3) containing CYX143, CYX144, CYX145, CYX146 and CYX147 plasmids in Example 5.

The pACYC-Trc-tesA and CYX134 plasmids were transformed into E. coli BL21 (DE3), the induced fermentation was conducted at 30° C. for 40 h and GC-MS detection was performed on the fermentation products. The results are shown in FIG. 2. In the strains transformed with the pACYC-Trc-tesA module only detected the production of fatty acids, which were generated from the hydrolysis of aliphatic acyl-ACP by thioesterase (TesA'). Meanwhile, after addition of the dox gene to the pACYC-Trc-tesA plasmid (CYX134), three aliphatic aldehydes,1-undecanal, tridecanal and pentadecenal were detected at retention times (RT) of 11.20 min, 14.73 min and 17.59 min, respectively. The three aliphatic aldehydes were generated by oxidation of α-Dox from free fatty acids of $C_{12}$, $C_{14}$ and $C_{16:1}$ in E. coli cells. The results confirmed the feasibility of a synthesis of odd numbered medium chain aliphatic alcohols and even numbered medium chain hydrocarbons in the present patent application, i.e., α-dioxygenase can synthesize odd numbered medium chain aliphatic aldehydes in *E. coli* and can provide precursors for synthesizing odd numbered medium chain aliphatic alcohols and even numbered medium chain aliphatic hydrocarbons.

In addition, in the strains transformed with CYX134 module, 1-undecanol, 1-tridecanol and 1-pentadecanol were also detected at the retention times (RT) of 12.37 min, 15.75 min and 18.80 min, respectively (as shown in FIG. 2B). These three aliphatic alcohols were the products of spontaneous reduction of aliphatic aldehydes with the corresponding carbon chain in the cells. The mass spectra profiles of the products are shown in FIG. 1C-H. The match factor and the reverse match factor of the respective substances were both 850 or more, and the accuracy of the odd numbered medium chain aliphatic aldehyde/alcohol molecules of the present invention was confirmed.

EXAMPLE 5

Selection of Aldehyde Reductase

Experiment Methods

1. Construction of plasmids: Different aldehyde reductases (AdhP, YjgB, YqhD, AdhE, Slr1192) were ligated into CYX134 plasmid. Specifically, CYX134 was taken as vector, restriction-digested with SpeI and BamHI, and purified. 28a-AdhP, 28a-YjgB, pET28a-YqhD, pET28a-AdhE, pET28a-Slr1192 were taken as templates, respectively, restriction-digested with XbaI and BamHI, gel-extracted and ligated to vector. See the specific fragment length in Table 6.

TABLE 6

Construction of the plasmids

| Name of the plasmid constructed | Vector | Restriction site of the vector | Length of the vector | Origin of the fragment | Restriction site of the fragment | Length of the fragment |
|---|---|---|---|---|---|---|
| CYX143 | CYX134 | SpeI | 6950 | 28A-AdhP | XbaI | 1036 |
| CYX144 | | BamHI | | 28A-yjgB | BamHI | 1038 |
| CYX145 | | | | 28A-yqhD | | 1275 |
| CYX146 | | | | 28A-AdhE | | 2687 |
| CYX147 | | | | 28A-slr119 | | 1122 |

2. Each plasmid was transformed into *E. coli* BL21 (DE3) strain by heat shock and screened on LB solid plate. The cells were all cultured in an incubator at 30° C., and the content of each antibiotic in the solid and liquid media was 34 μ/mL chloramphenicol.

3. The *E. coli* BL21 (DE3) strain transformed with each plasmid was subjected to fermentation, with the same method process as in Example 1.

4. Extraction of aliphatic alcohols, the method process was the same as in Example 1.

5. Detection of aliphatic alcohol extraction samples, the method process was the same as in Example 1.

Experiment Results

*E. coli* BL21 (DE3) was transformed with each plasmid and induced fermentation was conducted for 40 h at 30° C. The results of GC-MS analysis on the fermentation products are shown in FIG. 2. It can be seen that AdhE and AdhP do not have promotion effect on the production of odd numbered medium chain aliphatic alcohols, while YqdD, Slr1192 and YjgB further promote the *E. coli* synthesis of an odd numbered medium chain aliphatic alcohol proposed in this patent. Wherein YjgB has the most significant promotion effect on the production, with the production of total aliphatic alcohols increased from 35.2 mg/L to 68.3 mg/L.

Example 6

Selection of Aldehyde Decarbonylase

Experiment Methods

1. Construction of the plasmids: different aldehyde decarbonylases (CER1, AD9313, AD7942 and AD7310) were ligated into the CYX134 plasmid. Specifically, CYX134 was taken as vector, and pET28a-CER1, pET28a-AD9313, pET28a-AD7942 and pET28a-AD73102 were respectively taken as templates, restriction-digested, gel-extracted and ligated to vector. Vector restriction site, vector length, fragment restriction site, fragment length and other specific information are shown in Table 7.

TABLE 7

Information of plasmid construction

| Name | Vector name | Vector restriction site | Vector length | Origin of the fragment | Fragment restriction site | Fragment length |
|---|---|---|---|---|---|---|
| CYX148 | CYX134 | SpeI | 6950 | 28A-CER1 | XbaI | 1879 |
| CYX149 | | BamHI | | 28A-AD9313 | BamHI | 747 |
| CYX150 | | | | 28A-AD7942 | | 750 |
| CYX151 | | SpeI-SacI | 6950 | 28A-AD73102 | XbaI-SacI | 806 |

2. Each plasmid was transformed into *E. coli* BL21 (DE3) strain by heat shock and screened on LB solid plate. The cells were all cultured in an incubator at 30° C., and the content of each antibiotic in the solid and liquid media was 34 μg/mL chloramphenicol.

3. The *E. coli* BL21 (DE3) strain transformed with each plasmid was subjected to fermentation, with the same method process as in Example 1.

4. Extraction of aliphatic alcohols, the method process was the same as in Example 1.

5. Detection of aliphatic alcohol extraction samples, the method process was the same as in Example 1.

Experiment Results

Figure 3:
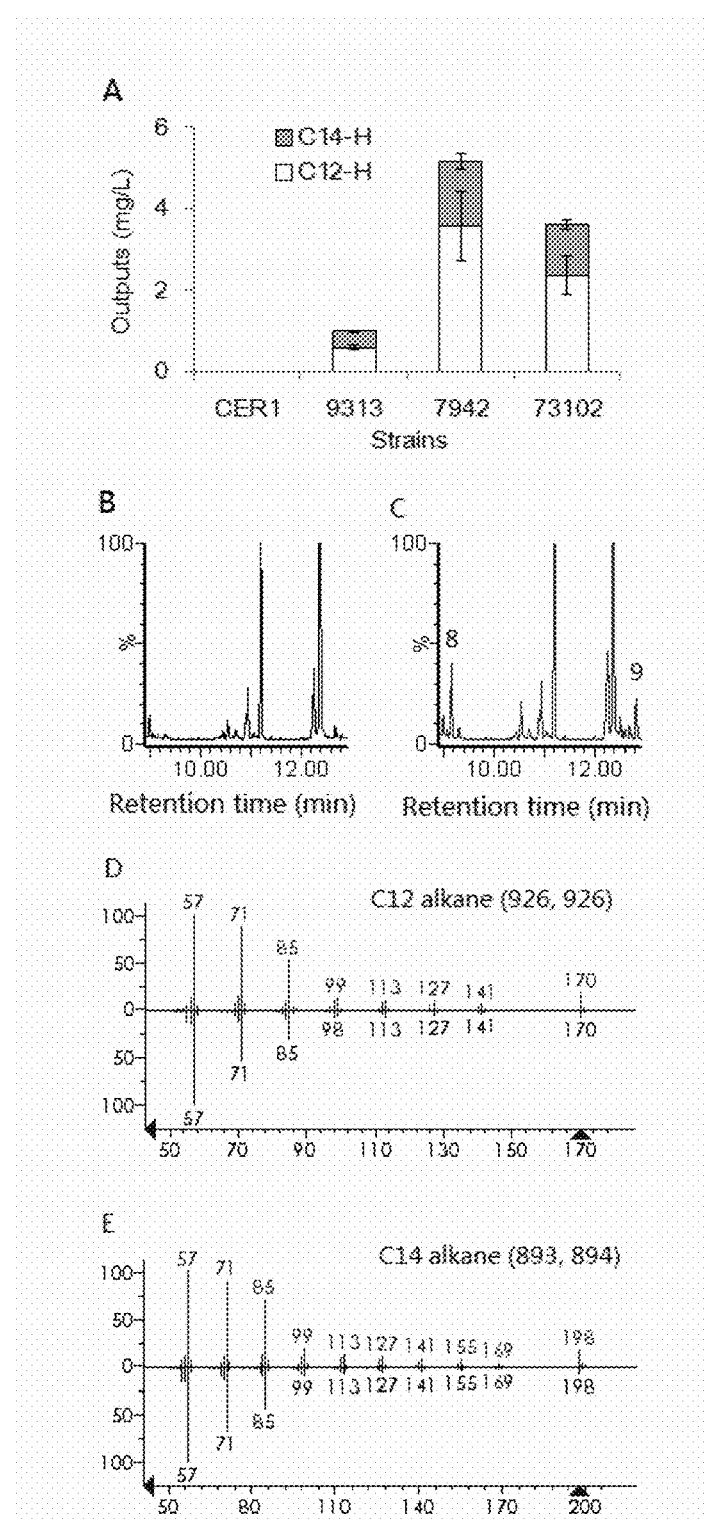
FIG. 3 shows the results of the aliphatic hydrocarbon output after induced fermentation at 30° C. for 40 h in *E. coli* BL21 (DE3) containing CYX148, CYX149, CYX150 and CYX151 plasmids in Example 6.

*E. coli* BL21 (DE3) was transformed with each plasmid and induced fermentation was conducted for 40 h at 30° C. The results of GC-MS analysis on the fermentation products are shown in FIG. 3. It can be seen that decarbonylase CER1 derived from *Arabidopsis thaliana* did not allow engineered *E. coli* to synthesize even numbered chain aliphatic hydrocarbons, while after expression of the three decarbonylases derived from cyanobacteria, all of the engineering *E. coli* synthesized the aliphatic hydrocarbons with chain length of C12 and C14, confirming the method for synthesizing medium chain aliphatic hydrocarbons using *E. coli* by the present patent. Wherein, it has the highest production, 5.2 mg/L, of the medium chain hydrocarbons when the decarbonylase AD7942 derived from *Nostoc flagelliform* was expressed. FIG. 3B shows the position of the aliphatic hydrocarbons in the gas chromatogram after transformed with the CYX151 plasmid. Wherein 8 was dodecane and 9 was tetradecane. The mass spectra of the respect products are shown in FIGS. 3D and E. The match factor and reverse match factor for each substance were both 850 or more, confirming the qualitative accuracy of the even numbered chain aliphatic hydrocarbon products of the present invention.

In summary, the invention provides a microbial synthesis pathway and a construction method of odd numbered medium chain aliphatic alcohols and even numbered medium chain hydrocarbons by synthetic biological means; the present invention also provides an engineered *E. coli* that prepares odd numbered medium chain aliphatic alcohols and even numbered medium chain hydrocarbons using the above-described pathway.

Example 7

Optimization of the Metabolic Flow Between α-Dioxygenase and Thioesterase

Experiment Materials

Plasmid pBAD33 was purchased from ATCC.

Experiment Methods

1. Construction of expression plasmids (YX210, YX211, YX212 and YX213) containing different promoters
1) The vector was pACYCDute-1 and amplified with the primer AflII-pACYC-fwd and the primer PstI-pACYC-rev in Table 8.
2) The fragment templates were pQE-80L, pKS1, pTrcHis2A and pBAD33, and amplified with the remaining primers in Table 8, ligated to vector to construct the plasmids YX210, YX211, YX212 and YX213. These plasmids have two promoters simultaneously, one promoter was T7 and the other promoter was T5, pLacUV5, Trc and BAD. The specific information of these plasmids is shown in Table 9.

2. Construction of the plasmids of thioesterase gene endogenous to *E. coli* controlled by the T7 promoter
1) The vectors were pACYCDute-1, YX210, YX211, YX212 and YX213, restriction-digested with NdeI and KpnI, and purified.
2) The fragment template was pKS1 plasmid, amplified with the primers NdeI-tesA-fwd and KpnI-tesA-rev (see Table 8 for primer sequences). After PCR, the products were restriction-digested and purified, and ligated to vector. The correct transformants were picked.

3. Construction of the plasmids of α-dioxygenase and endogenous thioesterase controlled by dual promoters without 6*His tag (YX220, YX232, YX233, YX234 and YX235)
1) The vectors were the five plasmids generated in step 2, with the polyclonal sites in the first promoter cleaved with NcoI and BamHI, and purified.
2) The fragment template was the synthetic dox gene, amplified with the primers NcoI-Dox-fwd and BamHI-SpeI-Dox-rev (see Table 8 for primer sequences), and the length after PCR was 1874; restriction-digested and purified, and ligated to vector, and the correct transformants were picked. The first promoter (T7, T5, pLacUV5, Trc and BAD) in YX220, YX232, YX233, YX234 and YX235 controls the dox gene without the 6*His tag and the second promoter (T7) controls the tesA' gene.

4. Construction of the plasmids of α-dioxygenase and endogenous thioesterase controlled by dual promoters containing 6*His tag (YX221, YX222, YX223, YX224 and YX225)
1) The vectors were the five plasmids generated in step 2, with the polyclonal sites in the first promoter cleaved with NcoI and BamHI, and purified.
2) The fragment template was the 21a-dox plasmid, restriction-digested with NcoI and BamHI, gel-extracted, ligated to vector, and the correct transformants were picked. The first promoter (T7, T5, pLacUV5, Trc and BAD) in YX221, YX222, YX223, YX224 and YX225 controls the dox gene containing the 6*His tag and the second promoter (T7) controls the tesA' gene.

5. Construction of plasmids containing α-dioxygenase controlled by T7, T5, pLacUV5, Trc and BAD promoters
1) The vectors were pACYCDute-1, YX210, YX211, YX212 and YX213, restriction-digested with NcoI and BamHI, and purified.
2) The fragment template was the synthetic dox gene, amplified with the primers NcoI-Dox-fwd and BamHI-SpeI-Dox-rev (see Table 8 for primer sequences); restriction-digested after PCR and purified, ligated to vector, and the correct transformants were picked.

6. Construction of plasmids containing dox-tesA' controlled by T7, T5, pLacUV5, Trc and BAD promoters (YX135, YX136, YX137, YX138 and YX140)
1) The vectors were the five plasmids generated in Step 5, restriction-digested with SpeI and BamHI, and purified.
2) The fragment template 21a-tesA was restriction-digested with XbaI and BamHI, gel-extracted, ligated to vector, and the correct transformants were picked. The first promoters (T7, T5, pLacUV5, Trc and BAD) in YX135, YX136, YX137, YX138 and YX140 control both the two genes dox and tesA'.

7. Construction of a plasmid containing the thioesterase gene endogenous to *E. coli* controlled by the T7, T5, pLacUV5, Trc and BAD promoters
1) The vectors were YX210, YX211, YX212 and YX213, restriction-digested with NcoI and BamHI, and purified.
2) The fragment template was pKS1, amplified with the primers NcoI-tesA-fwd and BamHI-SpeI-tesA-rev (see Table 8 for primer sequences); restriction-digested after PCR and purified, ligated to vector, and the correct transformants were picked.

8. Construction of plasmids containing tesA'-dox controlled by T7, T5, pLacUV5, Trc and BAD promoters (YX131, YX132, YX133, YX134 and YX130)
1) The vectors were the five plasmids generated in Step 7, restriction-digested with SpeI and BamHI, and purified.
2) The fragment template 21a-Dox was restriction-digested with XbaI and BamHI, gel-extracted, ligated to vector, and the correct transformants were picked. The first promoters (T7, T5, pLacUV5, Trc and BAD) in YX131, YX132, YX133, YX134 and YX130 control both the two genes tesA' and dox.

TABLE 8

The primers needed in optimization of the metabolic flow between α-dioxygenase and thioesterase

| Primer | number | Sequence* |
|---|---|---|
| AflII-pACYC-fwd | SEQ ID No. 42 | GGCCCTTAAGTCGAACAGAAAGTA |
| PstI-pACYC-rev | SEQ ID No. 43 | TATCTGCAGCATAAGGGAGAGCGTCGAGA |
| PstI-pT5-fwd | SEQ ID No. 44 | AAACTGCAGCCTTTCGTCTTCACCTCGAG |
| SacI-MCS-rev | SEQ ID No. 45 | TTGAGCTCGCATGCGGATCCTT |
| PstI-pLacUV5-fwd | SEQ ID No. 46 | AATCTGCAGCCGATGGCGCGCCGA |
| AflII-rrnB-rev | SEQ ID No. 47 | TCGACTTAAGCGTTCACCGACAAACAACAG |
| PstI-Gibson-pHisTrc-fwd | SEQ ID No. 48 | TCTCGACGCTCTCCCTTATGCTGCAGACATCATAACGGTTCTGGCA |
| AflII-Gibson-rrnBT1-rev | SEQ ID No. 49 | TACGATTACTTTCTGTTCGACTTAAGGGCGGATTTGTCCTACTCAG |
| PstI-Gibson-araC-fwd | SEQ ID No. 50 | TCTCGACGCTCTCCCTTATGCTGCAGCCTGTCAAATGGACGAAG |
| NdeI-tesA-fwd | SEQ ID No. 51 | CGGATCATATGGCGGACACGTTATTGAT |
| KpnI-tesA-rev | SEQ ID No. 52 | CCCCGGTACCTTATGAGTCATGATTTACTA |
| NcoI-Dox-fwd | SEQ ID No. 53 | GCGCCATGGGCAGCGGTTTATTCAA |

*Linear underlined sequences are the restriction sites, and bold, italic sequences are the start codon or stop codon.

TABLE 9

Information of expression plasmids containing different promoters

| Vectors | Replication origin | Promoters | Resistance |
|---|---|---|---|
| YX210 | p15A | $P_{T5}$ and $P_{T7}$ | Cam |
| YX211 | p15A | $P_{lacUV5}$ and $P_{T7}$ | Cam |
| YX212 | p15A | $P_{Trc}$ and $P_{T7}$ | Cam |
| YX213 | p15A | $P_{BAD}$ with areC operon, and $P_{T7}$ | Cam |

9. Each plasmid was transformed into *E. coli* BL21 (DE3) strain by heat shock and screened on LB solid plate. The cells were all cultured in an incubator at 30° C., and the content of each antibiotic in the solid and liquid media was 34 μg/mL chloramphenicol.

10. The *E. coli* BL21 (DE3) strains transformed with each of the plasmids were subjected to fermentation, with the same method process as in Example 1.

11. Extraction of aliphatic alcohols, the method process was the same as in Example 1.

12. Detection of the aliphatic alcohol extraction sample, the method process was the same as in Example 1.

Figure 4:
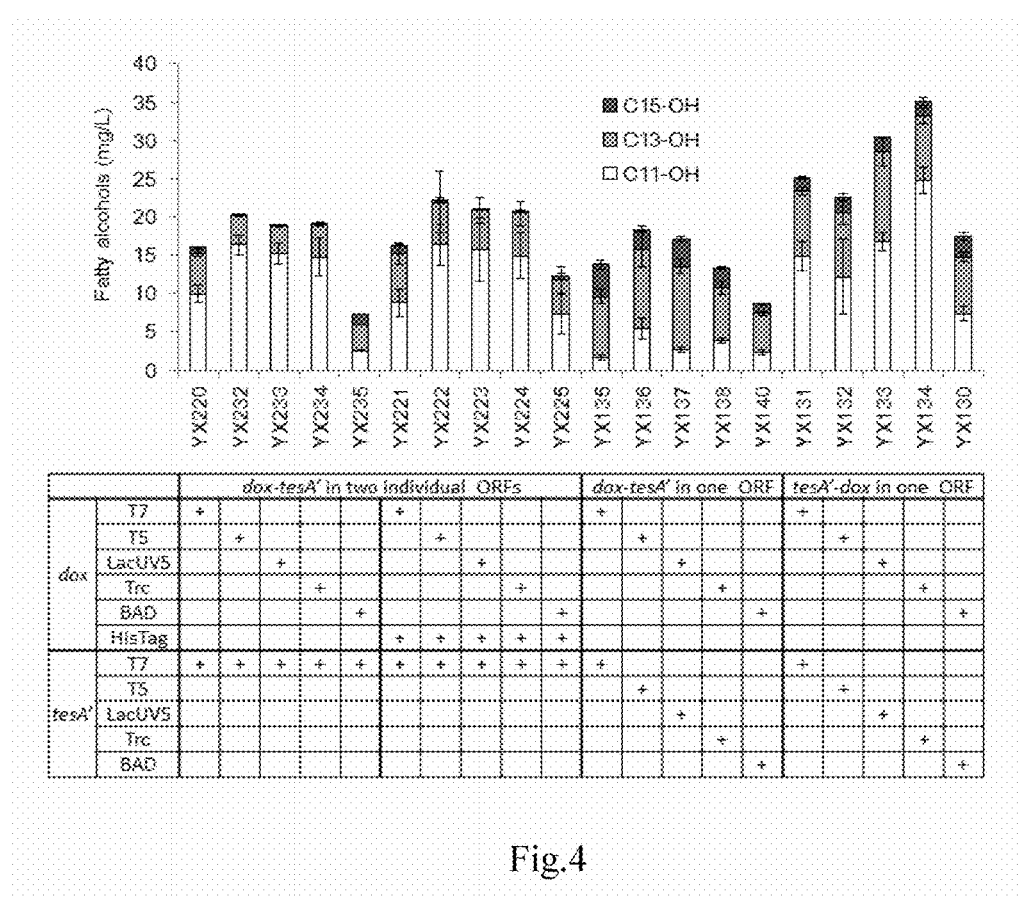
FIG. 4 shows the results of the optimization of the metabolic flow between α-dioxygenase and endogenous thioesterase in Example 7.

Experiment Results:

The *E. coli* BL21 (DE3) were transformed with each plasmid and induced fermentation was conducted for 40 h at 30° C. The results of GC-MS analysis on the fermentation products are shown in FIG. 4. The metabolic flow between TesA' and α-Dox was divided into two parts for optimization.

Firstly, TesA' and α-Dox were expressed in two open reading frames (ORFs). TesA' was controlled by the T7 promoter and α-Dox was expressed with five different promoters. When α-Dox was under the control of T7 promoter with the strongest expression of or BAD promoter with the weakest expression, the amount of aliphatic alcohol production was relatively low. When the expression intensity of α-Dox was moderate (controlled by T5, LacUV5 and Trc promoters), the output of aliphatic alcohols was relatively high. This indicated that the expression intensities between TesA' and α-Dox were too much different from each other, and when the expression of α-Dox was slightly less than TesA', the metabolic flow was relatively balanced. In addition, addition of the 6*His tag at the N-terminus of the α-Dox protein did not increase the output of aliphatic alcohols at the same intensity of expression, suggesting that α-Dox was stable in the (post) transcriptional and/or (post) translational stages.

Secondly, TesA' and α-Dox were expressed in one open reading frame to optimize the expression intensities of the two genes. In the construction of plasmids, dox-tesA' and tesA'-dox constructs were constructed respectively. When the two genes were simultaneously expressed in one open reading frame, the gene closer to the promoter will have stronger expression intensity. It can be seen from FIG. 4 that the aliphatic alcohol output was higher when the tesA' was closer to the promoter. This was consistent with the conclusion of the first optimization that TesA' expression intensity needs to be slightly higher than α-Dox. In addition, the expression intensity of tesA'-dox should not be too high or too low, and when under the control of Trc promoter, the highest output of aliphatic alcohol was reached (35.2 mg/L).

The CYX134 plasmid in Example 4 was the plasmid most optimized in the metabolic flow between tesA' and α-Dox in this example (CYX is equivalent to YX).

Example 8

Confirmation of the Extensive Substrate Selectivity and Controllability of α-Dioxygenase in Cells Experiment Methods
1. Construction of fatty acid pathway over-expressing plasmids containing different thioesterases (YX101, YX102 and YX103)

1) The vector was pACYCDute-1, restriction-digested with EcoRI and SacI, or restriction-digested with SalI and HindIII, and purified.
2) The fragment templates were three different thioesterase genes: tesA' gene in pKS1 (derived from *Escherichia coli*), or synthetic bte (derived from *Umbellularia californica*) and BnFatA gene (derived from *Brassica napus*), and different gene fragments were amplified by corresponding primers (the primer sequences are shown in Table 10, and the names of the fragments and the length after PCR are shown in Table 11), restriction-digested, purified, and ligated to vector.
3) Colony PCR with the primer Duet-seq-F and the primer pACYCDuet-R, with the correct length shown in Table 11.

Construction of aliphatic alcohol synthesis pathway over-expressing plasmids containing different thioesterases (YX135, YX104 and YX105)
1) The vectors were YX101, YX102 or YX103, restriction-digested with NcoI and BamHI, and purified.
2) The fragment template was the synthetic dox gene, amplified with the primers NcoI-Dox-fwd and BamHI-SpeI-Dox-rev, with the length after PCR of 1874, restriction-digested, purified, ligated to vector, and the correct transformants were picked.

TABLE 10

The list of primers needed to confirm the extensive substrate selectivity and controllability of α-dioxygenase possesses in cells

| Primer | number | Sequence* |
|---|---|---|
| EcoRI-RBS-tesA-fwd | SEQ ID No. 54 | AGGGAATTCAAAGGAGGCCATCCT*ATG*GCGGACACGTTATTGAT |
| SacI-tesA-rev | SEQ ID No. 55 | CCCGAGCTC*TTA*TGAGTCATGATTTAC |
| SalI-RBS-BTE-fwd | SEQ ID No. 56 | GGAAAGTCGACAAGGAGGATTATA*ATG*GCGCTGGAATGGAAACC |
| HindIII-BET-rev | SEQ ID No. 57 | TTTTGAAGCTT*TTA*CACACGCGGTTCCGCCG |
| SalI-BnFatA-RBS-fwd | SEQ ID No. 58 | GGAAAGTCGACAAGGAGGCCATCCT*ATG*CTGAAACTGAGCTGTAA |
| HindIII-BnFatA-rev | SEQ ID No. 59 | CAGGGAAGCTT*TTA*GCGGGAGGATTTTTTACGCCA |

*Linear Underlined sequences are the restriction sites, **bold, *italic*** sequences are the start codon or stop codon, and wavy underline sequences are RBS.

TABLE 11

| Name of the constructed plasmid | Name of the fragment | Fragment length | Colony PCR length |
|---|---|---|---|
| YX101 | pKS1 | 585 | 835 |
| YX102 | BTE | 941 | 1187 |
| YX103 | BnFatA | 1137 | 1383 |

3. YX101, YX102 and YX103 plasmids were respectively transformed into E. coli BL21 (DE3) strain by heat shock and screened on LB solid plate. All the cells were cultured in an incubator at 30° C., and the content of each antibiotic in the solid and liquid media was 34 μg/mL of chloramphenicol.

4. The E. coli BL21 (DE3) strain transformed with each plasmid was subjected to fermentation as in Example 1.

5. Extraction of fatty acid: 0.5 mL of medium fermented at 30° C. for 40 h after induction was sampled, and 50 μL of hydrochloric acid and 25 μg of heptadecanoic acid were added as internal standards; 0.5 mL ethyl acetate was added, vortexed for 5 min, and centrifugated at 15000 rpm for 2 min (the same hereinafter); the top-layer organic phase was aspirated, 0.5 mL ethyl acetate was added to the bottom-layer solution again, vortexed for 5 min, and centrifugated to obtain the top-layer organic phase; the two parts of extracts were combined, and the extracted free fatty acids were methylated by addition of 20 μl of diazomethane, 1 μL of hydrochloric acid and 9 μL of methanol, and the mixture was blow-dried with nitrogen gas after two hours of reaction; the evaporated product (fatty acid methyl ester, FAME) was dissolved in 0.5 mL of n-hexane, and filtered with 0.22 μm nylon membrane. Samples were stored in a −80° C. refrigerator prior to injecting.

6. Detection of fatty acid extraction samples, the method process was the same as that of Example 1 for the detection of aliphatic alcohols.

7. YX135, YX104 and YX105 plasmids were respectively transformed into E. coli BL21 (DE3) strain by heat shock and screened on LB solid plate. The cells were all cultured in an incubator at 30° C., and the content of each antibiotic in the solid and liquid media was 34 μg/mL of chloramphenicol.

8. The E. coli BL21 (DE3) strain transformed with each plasmid were subjected to fermentation, with the same method process as in Example 1.

9. Extraction of aliphatic alcohols, the method process was the same as in Example 1.

10. Detection of aliphatic alcohol extraction samples, the method process was the same as in Example 1.

Experiment Results

Figure 5:
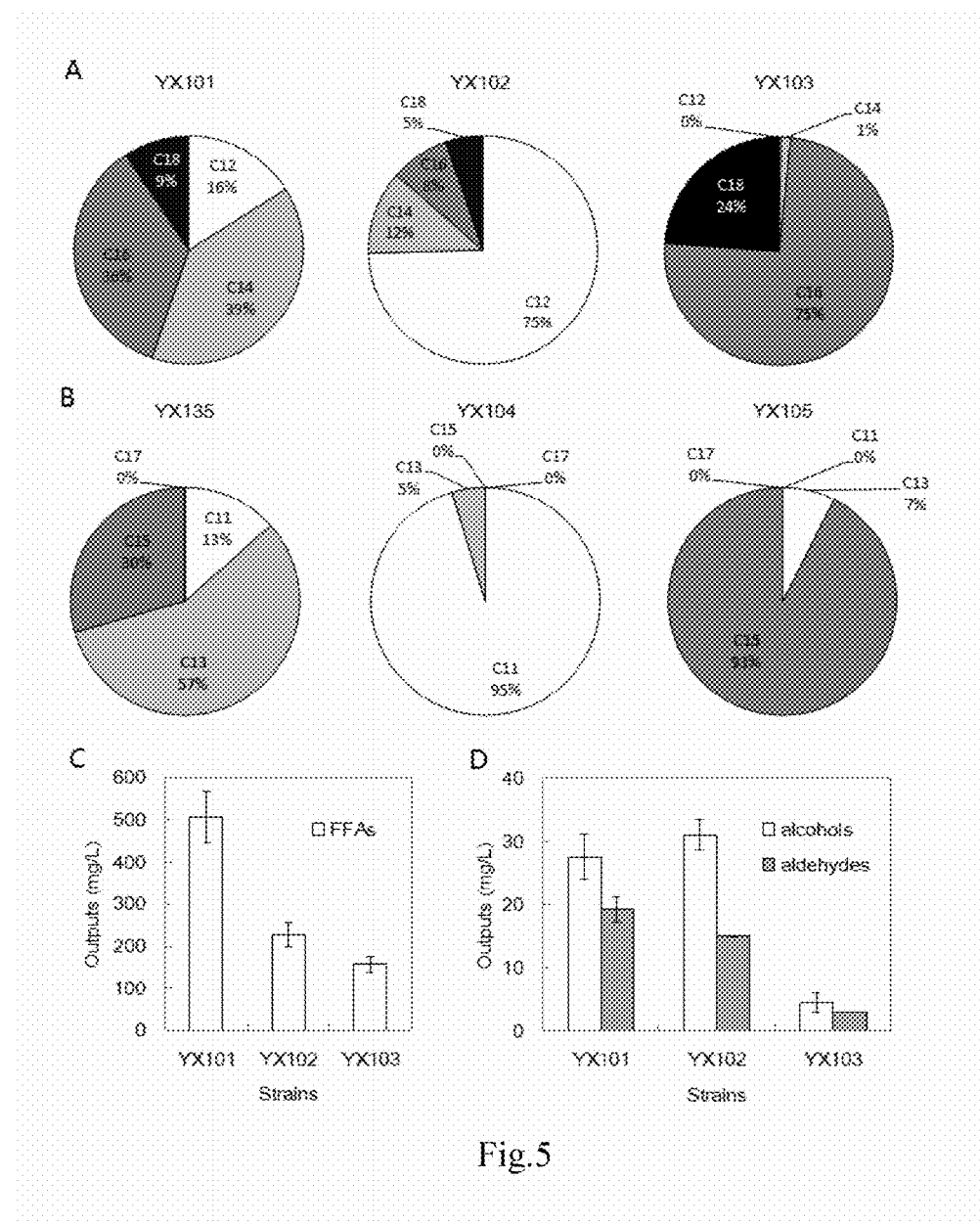
FIG. 5 shows that it is confirmed that α-dioxygenase possesses extensive substrate selectivity and controllability in cell in Example 8.

The E. coli containing YX101, YX102 or YX103 plasmids was subjected to fermentation, and the results are shown in FIG. 5. The engineered strains over-expressing TesA', BTE or BnFatA synthesized fatty acids of $C_{14}/C_{16}$ (39%/36%), $C_{12}$ (75%) and $C_{16}/C_{18}$ (75%/24%) as the major products, respectively. When αDOX was co-over-expressed with thioesterase, the different engineered strains synthesized $C_{13}/C_{15}$ (57%/30%), $C_{11}$ (95%), as well as $C_{15}$ (93%) of aliphatic aldehydes+aliphatic alcohols as the major products. This indicates that the ratio of the product of the aliphatic aldehydes+the aliphatic alcohols after over-expression of αDOX matches the ratio of the product of the precursor fatty acids. The only exception was when BnFatA was over-expressed, there was 24% of the C18 fatty acids, however, no corresponding C17 aliphatic aldehyde/alcohol was produced after over-expression of αDOX. These results indicate that αDOX was capable of oxidizing C12-C16 fatty acids in the cell. In this range, it was possible to convert fatty acid substrate with different chain lengths into the corresponding aliphatic aldehyde, indicating that the controllability was possessed by αDOX and the present system.

Example 9

Regulation of the Expression Intensity of the Upstream Fatty Acid Synthesis Pathway to Increase the Synthesis Ability of Odd Numbered Medium Chain Aliphatic Alcohols Experiment Methods 1. Construction of an upstream fatty acid pathway over-expression plasmids 1) The vector was pTrcHis2A, restriction-digested with NcoI and BamHI, and purified.

2) The fragment template was E. coli MG1655 genome, amplified with primers NcoI-GCG- * -fwd and BamHI-SpeI- * -rev for different gene fragments (*** represents a gene name) (see primer sequence in Table 12, and the fragment name and length after PCR shown in Table 13, wherein substitution of XhoI restriction site was required in FabD and substitution of NcoI restriction site was required in FabG), gel-extracted, restriction-digested with NcoI and BamHI, purified, and ligated to vector.

3) Colony PCR with primer pTrcHis2A-F and primer pTrcHis2A-R, with the correct length shown in Table 13.

TABLE 12

| The list of primers needed in over-expression of fatty acid pathway genes | | |
|---|---|---|
| Primer | number | Sequence* |
| NcoI-GCG-fabD-fwd | SEQ ID No. 60 | CGTTCCATGGCGACGCAATTTGCATTTGTGTT |
| BamHI-SpeI-fabD-rev | SEQ ID No. 61 | AAGGATCCGAATACTAGTTAAAGCTCCAGCGCCGCTGCCATCGCTGA |
| NcoI-GCG-fabG-fwd | SEQ ID No. 62 | GGGTCCATGCGAATTTTGAAGGAAAAATCGC |

TABLE 12-continued

The list of primers needed in over-expression of fatty acid pathway genes

| Primer | number | Sequence* |
|---|---|---|
| BamHI-SpeI-fabG-rev | SEQ ID No. 63 | AA<u>GGATCC</u>GAAT<u>A</u><u>CTAG</u>*TTA*GACCATGTACATCCCGCCG |
| NcoI-fabA-fwd | SEQ ID No. 64 | GGT<u>CC</u>*ATG*GTAGATAAACGCGAATC |
| BamHI-SpeI-fabA-rev | SEQ ID No. 65 | AA<u>GGATCC</u>GAAT<u>A</u><u>CTAG</u>*TTA*GAAGGCAGACGTATCCG |
| NcoI-GCG-fabI-fwd | SEQ ID No. 66 | GGT<u>CC</u>*ATG*GGTTTTCTTTCCGGTAA |
| BamHI-SpeI-fabI-rev | SEQ ID NO. 67 | AA<u>GGATCC</u>GAAT<u>A</u><u>CTAG</u>*TTA*TTTCAGTTCGAGTTCGT |
| NcoI-GCG-fabB-fwd | SEQ ID No. 68 | AAT<u>CC</u>*ATG*GCGAAACGTGCAGTGATTACTGG |
| BamHI-SpeI-fabB-rev | SEQ ID No. 69 | AA<u>GGATCC</u>GAAT<u>A</u><u>CTAG</u>*TTA*ATCTTTCAGCTTGCGCATT |
| NcoI-fadR-fwd | SEQ ID No. 70 | GGT<u>CC</u>*ATG*GTCATTAAGGCGCAAAG |
| BamHI-fadR-rev | SEQ ID No. 71 | GA<u>GGATCC</u>GAAT<u>A</u><u>CTAG</u>*TTA*TCGCCCCTGAATGGCTA |

*Linear underlined sequences are the restriction sites, and bold, italic sequences are the start codon or stop codon.

TABLE 13

Detailed information of the fragments

| Name of the constructed plasmid | Name of the fragment | Fragment length | Colony PCR length |
|---|---|---|---|
| FabA | fabA | 534 | 863 |
| FabI | fabI | 814 | 1133 |
| FabG | fabG | 761 | 1082 |
| FabD | fabD | 955 | 1277 |
| FabB | fabB | 1246 | 1568 |
| FadR | fadR | 735 | 1055 |

2. Knockout of the fadD and fadE genes in the β-oxidation pathway

1) Primer sequences for homologous recombination are shown in Table 14. The chloramphenicol was amplified from pKD3 plasmids with these two primers, the products were identified by agarose gel electrophoresis, and PCR gel-extraction products were recovered by agarose gel DNA recovery kit.

2) The plasmid pKD46 was transformed into *E. coli* BL21 (DE3) and the bacteria were cultured overnight in LB liquid medium at 30° C. The activated bacteria were inoculated into a liquid medium containing 10 mmol/L of L-arabinose in a ratio of 1:100; when the bacterial $OD_{600}$ reaches 0.5-0.6, pre-cooled on ice for 10 min, and centrifuged at 4° C., 4000 rpm for 5 min (the same hereinafter), followed by 3 times of centrifugation and washing with 10% chilling glycerol, concentrated 100-fold to electro-transfer competent cells, with 100 μL for each tube, and stored in −80° C. refrigerator for use.

3) Electroporator 2170 (Eppendorf, Germany) (0.1-cm chambers) was employed to transform the PCR-gel-extracted products in step 1) (10-100 ng) into competent BL-46 cells which were subjected to 1800 V electric shock for 5-6 ms, followed by addition of 1 mL antibiotic-free-LB medium, recovered at 37° C., 150 rpm for 3-4 h, and thereafter half of the cells were plated on LB plate medium containing 25 μg/mL chloramphenicol, with the remaining cells standing overnight at room temperature. If there was still no strain growing in the chloramphenicol plate after 24 h, these remaining cells were re-plated.

4) Single colonies in the plate of step 3) were picked, and colony PCR was conducted to verify whether the fadE gene in the genome had been substituted with chloramphenicol.

5) The correct transformants verified in step 4) were inoculated into 2 mL chloramphenicol LB medium and cultured at 43° C. for 12 h to delete the pKD46 plasmid. After streaking, the same single colony was picked and plated on ampicillin and chloramphenicol plates simultaneously, and cultured at 30° C. for 24 h, and if the same single colony grows in the chloramphenicol plate while not in the ampicillin plate, pKD46 was completely deleted.

6) The transformants with pKD46 deleted were inoculated and prepared into electroporation competent cells, and transformed with pCP20 plasmid; after recovered in 1 mL of antibiotic-free medium at 30° C. for 3-4 h, 100 μL was aspirated and inoculated into 2 mL of duel-antibiotic medium of ampicillin and chloramphenicol and cultured overnight at 30° C., followed by inoculation into antibiotic-free medium with a ratio of 1:200, cultured at 43° C. till stable phase and streaked on an antibiotic-free LB plate; single colonies were picked and streaked respectively on ampicillin plates and chloramphenicol plates to verify the ejection of chloramphenicol in chromatin and loss of pCP20 plasmid. PCR and sequencing verification were also performed.

TABLE 14

The list of primers needed for knockout of fadD and fadE genes in E. coli BL21 (DE3) genome

| Primer | number | Sequence* |
|---|---|---|
| fadE-pKD3-fwd | SEQ ID No. 72 | TATCATCACAAGTGGTCAGACCTCCTACAAGTAAGGGGCTTT TCGTT*ATG*TGTGTAGGCTGGAGCTGCTT |
| fadE-pKD3-rev | SEQ ID No. 73 | AAACGGAGCCTTTCGGCTCCGTTATTCAT*TTA*CGCGGCTTCAA CTTTCCGCATATGAATATCCTCCTTAG |
| fadD-pKD3-fwd | SEQ ID No. 74 | CATTTGGGGTTGCGATGACGACGAACACGCATTTTAGAGGTG AAGAA*TTG*TGTGTAGGCTGGAGCTGCTT |
| fadD-pKD3-rev | SEQ ID No. 75 | TAACCGGCGTCTGACGACTGACTTAACAC*TCA*GGCTTTATTGT CCACTTTCATATGAATATCCTCCTTAG |

*Sequences wherein 50-nt was homologous to both ends of the genome needed to be knocked out were indicated by dashed underline, and bold, italic sequences were the start codon or stop codon.

3. CYX144 plasmid and one of the plasmids constructed in method 1 were transformed into *E. coli* BL21 (DE3) strain by heat shock and screened on LB solid plate. All the cells were cultured in an incubator at 30° C. The content of each antibiotic in the solid and liquid media was 34 μg/mL chloramphenicol and 100 μg/mL ampicillin.

4. The *E. coli* BL21 (DE3) strain transformed with each plasmid were subjected to fermentation, with the same method process as in Example 1. When the CYX144 and fab genes were co-transformed into *E. coli* BL21 (DE3) strain for fermentation, the IPTG concentration was divided into three concentrations, 1 mM, 0.1 mM and 0.01 mM, for induction.

5. Extraction of aliphatic alcohols, the method process was the same as in Example 1.

6. Detection of aliphatic alcohol extraction samples, the method process was the same as in Example 1.

Experiment Results

Figure 6:
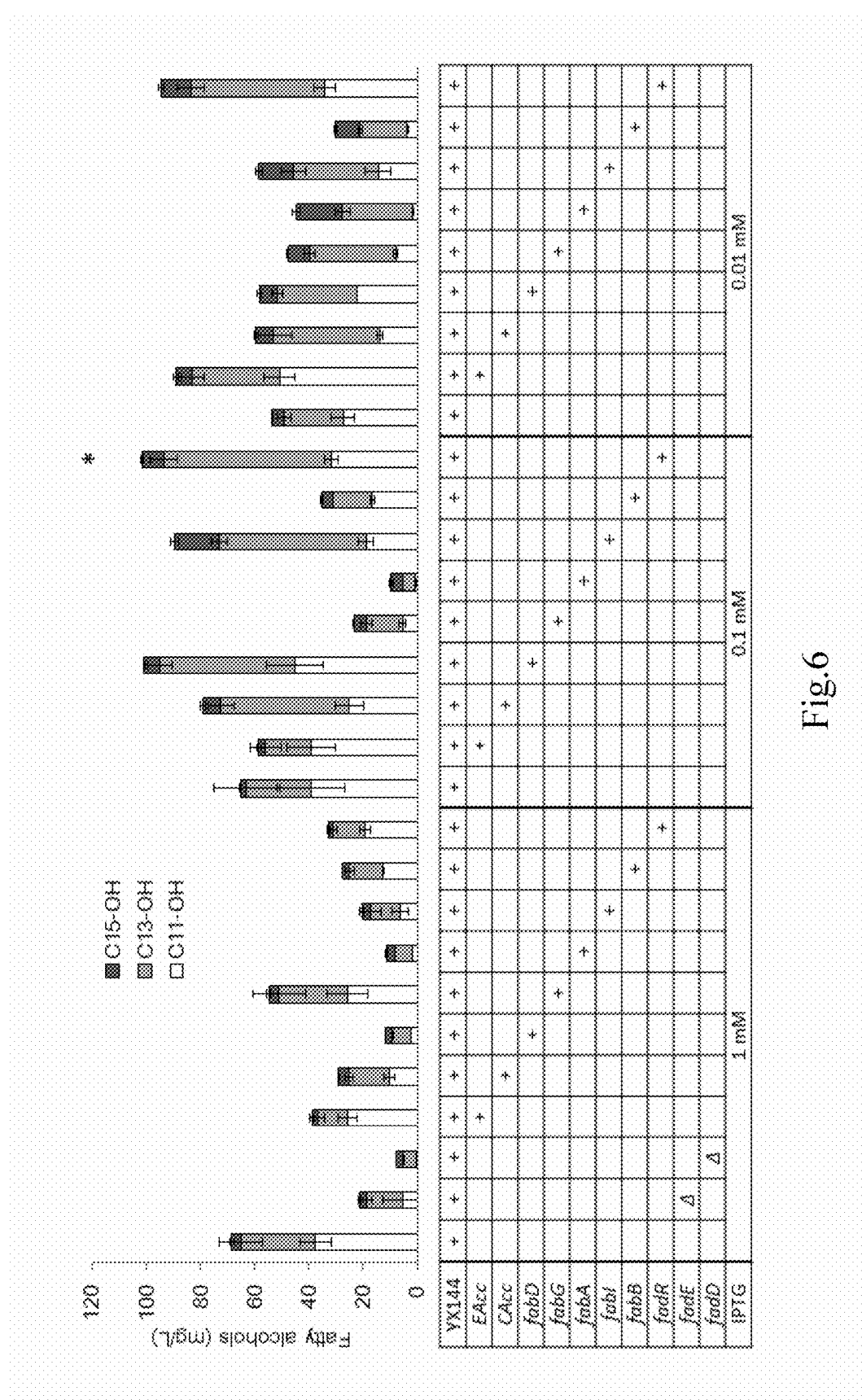
FIG. 6 shows the results for adjusting the expression intensity of the upstream fatty acid synthesis pathway to increase the synthesis ability of the odd numbered medium chain aliphatic alcohols in Example 9.

Each plasmid was transformed into *E. coli* BL21 (DE3) and the bacteria were induced to ferment for 40 h at 30° C. The results of GC-MS analysis on fermentation products are shown in FIG. 6. When the IPTG concentration was 1 mM, none of the genes in the over-expressed fatty acid synthesis pathway could enhance the synthesis ability of aliphatic alcohol; blocking of the fatty acid β-oxidation pathway by knockout of the fadD or fadE gene also did not promote the synthesis of aliphatic alcohol. However, when the concentration of the inducer IPTG was reduced to 0.1 mM, over-expression of acetyl-CoA carboxylase (ACC), FabD, FabI and FadR was capable of significantly increasing the output of aliphatic alcohols. For example, when FabD or FadR was co-over-expressed with CYX144, the output of odd numbered chain aliphatic alcohols was capable of being increased from 65.1 mg/L to 100.8 mg/L or 101.5 mg/L. When the concentration of IPTG was 0.01 mM, similarly, the overexpression of ACC, FabD, Fab I and FadR was capable of promoting the output of aliphatic alcohols. When FadR was co-over-expressed with CYX144, the output of aliphatic alcohols was 77.1% higher than that when CYX144 was over-expressed alone.

Example 10

Fed-Batch Fermentation

Experiment Methods:

1. CYX144 and FadR plasmids were transformed into *E. coli* BL21 (DE3) strain by heat shock and the bacteria were cultured overnight on LB solid plate at 30° C.; the recombinant single colonies were inoculated into 2 mL of LB medium and cultured at 30° C. until OD reached 2.5-4, and transferred to 20 mL of M9 medium at a ratio of 1:100, cultured at 30° C. until OD reached 2.5-4 and then transferred to 800 mL of M9 medium at a ratio of 1:100. When OD reached 2.5-4, the culture medium was centrifuged and concentrated to 50 mL and inoculated to 2.5 L fermentor for fed-batch fermentation. When the OD reached 15, induction was performed with 10 μM IPTG. Sampled for every 4 h, with 15 mL each time for analysis on cell density, glycerol, acetic acid, aliphatic alcohol concentrations. The content of each antibiotic in the solid and liquid media was 34 μg/mL of chloramphenicol and 100 μg/mL of ampicillin.

2. Cell densities were measured with a TU-1810 UV-Vis spectrophotometer (Beijing Purkinje General Instrument Co., Ltd.) at a wavelength of 600.

3. Measurement of glycerol and acetic acid concentrations: 1 mL of fermentation broth was centrifuged at 12,000 rpm for 10 min, and the supernatant was filterd with 0.22 μm filtration membrane and diluted as appropriate, or directly injected into HPLC for separation and detection. HPLC was Waters e2695, the detector was a 2414 RI differential detector, and the chromatographic column was Aminex HPX-87H column (BioRad, CA); the column temperature was maintained at 65° C. and the mobile phase was 5 mM dilute sulphuric acid aqueous solution with a flow rate of 0.6 mL/min.

4. Extraction of aliphatic alcohols, the method process was the same as in Example 1.

5. Detection of aliphatic alcohol extraction samples, the method process was the same as in Example 1.

Experiment Results

Figure 7:
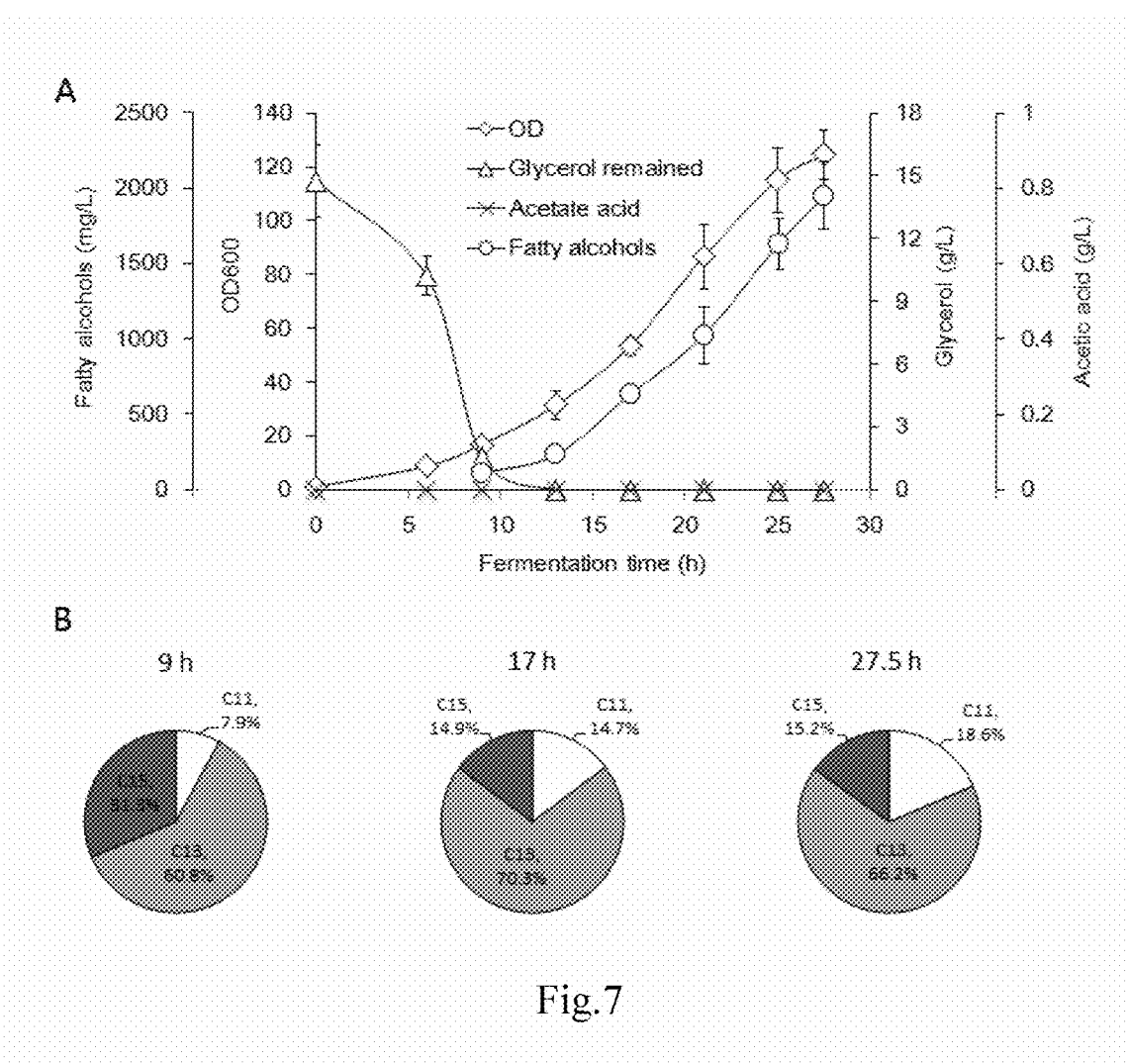
FIG. 7 shows the results of fed-batch fermentation in Example 10.

As shown in FIG. 7, after 18.5 h of induction, the yield of fatty alcohol reached 1.95 g/L, the OD value was 124.5 and the productivity was 0.105 g/L/h. The rates of glycerol consumption and addition were almost the same during fermentation, without generation of acetic acid. During the process of fermentation, the proportion of aliphatic alcohols with different chain length was almost constant over time, and at the end of fermentation, the proportions of C11, C13 and C15 fatty alcohols were 18.6%, 66.2% and 15.2%, respectively.

The gene, the encoded protein and use thereof, the gene element, the method for synthesizing an odd numbered medium chain aliphatic aldehyde, and the method for synthesizing an even numbered medium chain aliphatic hydrocarbon according to the present invention are described above in detail. The principles and embodiments of the present invention have been described using specific examples, and the description of the above examples is only for helping understanding the method of the present invention and the core idea thereof. It should be noted that a number of improvements and modifications of the present invention can be made by those skilled in the art without departing from the principles of the present invention, these improvements and modifications also fall within the protection scope of the present invention as defined by the claims of the present invention.

The invention claimed is:

1. A method for synthesizing an odd numbered C8-C15 aliphatic alcohol through an aliphatic aldehyde, comprising using
   a synthetic polynucleotide encoding α-dioxygenase which has an amino acid sequence identical to the amino acid sequence which the nucleotide sequence set forth in SEQ ID NO: 1 encodes, and
   a synthetic polynucleotide encoding aldehyde reductase which has an amino acid sequence identical to the amino acid sequence which yjgB gene set forth in SEQ ID NO: 76 encodes.

2. The method according to claim 1, wherein the aliphatic aldehyde is an odd numbered C8-C15 aliphatic aldehyde.

3. A vector comprising the synthetic polynucleotide according to claim 1.

4. An isolated host cell comprising the vector according to claim 3.

5. The isolated host cell according to claim 4, wherein the isolated host cell is *Escherichia coli*.

6. A polynucleotide element for synthesizing the odd numbered C8-C15 aliphatic alcohol, comprising
   a synthetic polynucleotide encoding α-dioxygenase which has an amino acid sequence identical to the amino acid sequence which the nucleotide sequence set forth in SEQ ID NO: 1 encodes,
   a synthetic polynucleotide encoding aldehyde reductase which has an amino acid sequence identical to the amino acid sequence which yjgB gene set forth in SEQ ID NO: 76 encodes, and
   a polynucleotide sequence set forth in SEQ ID NO: 77 encoding a thioesterase.

\* \* \* \* \*